United States Patent [19]

Spies

[11] Patent Number: 5,736,334
[45] Date of Patent: Apr. 7, 1998

[54] NUCLEOTIDE SEQUENCES AND PROCESS FOR AMPLIFYING AND DETECTION OF HEPATITIS B VIRAL DNA

[75] Inventor: Uwe Spies, Limburg, Germany

[73] Assignee: Abbott Laboratories, Abbott Park, Ill.

[21] Appl. No.: 758,626

[22] Filed: Nov. 27, 1996

Related U.S. Application Data

[63] Continuation of Ser. No. 422,018, Apr. 12, 1993, abandoned, which is a continuation of Ser. No. 90,755, Jul. 13, 1993, abandoned.

[51] Int. Cl.$^6$ .............................. C12Q 1/68; C07H 21/04
[52] U.S. Cl. ................................... 435/6; 536/24.33
[58] Field of Search .................. 435/5, 6; 536/24.3, 536/24.32, 24.33

[56] References Cited

U.S. PATENT DOCUMENTS

| | | | |
|---|---|---|---|
| 4,562,159 | 12/1985 | Shafritz | 436/5 |
| 4,683,195 | 7/1987 | Mullis | 435/6 |
| 4,683,202 | 7/1987 | Mullis | 435/91.2 |
| 5,124,246 | 6/1992 | Urdea et al. | 435/6 |
| 5,348,853 | 9/1994 | Wang et al. | 435/6 |
| 5,573,907 | 11/1996 | Carrino et al. | 435/6 |

FOREIGN PATENT DOCUMENTS

| | | |
|---|---|---|
| 0 229 701 | 7/1987 | European Pat. Off. . |
| 0 320 308 | 12/1988 | European Pat. Off. . |
| WO 91/10746 | 7/1991 | WIPO . |
| WO 93/13120 | 7/1993 | WIPO . |

OTHER PUBLICATIONS

Barany (1991) Proc. Natl. Acad. Sci. USA 88:189–193.
Ono et al. (1983) Nucleic Acids Res. 11:1747–1757.
Galibert et al. (1979) Nature 281:646–650.
Kobayashi et al. (1984) Gene 30:227–232.
Okamoto et al. (1986) J. Gen. Virol. 67:2305–2314.

*Primary Examiner*—George C. Elliott
*Assistant Examiner*—Robert Schwartzman
*Attorney, Agent, or Firm*—Thomas D. Brainard; Paul D. Yasger

[57] ABSTRACT

Short nucleotide sequences of hepatitis B virus useful for the determination of the presence and type of hepatitis B virus present in a test sample. The sequences provided can be amplified by various DNA hybridization techniques including a modified polymerase chain reaction or ligase chain reaction. The sequences provided also can be hybridized by standard dot- or replica-blot procedures. Methods and kits also are provided for the detection of hepatitis B virus in a test sample and the determination of the type of hepatitis B virus present in the test sample.

12 Claims, 5 Drawing Sheets

NUCLEOTIDE SEQUENCES AND PROCESS FOR AMPLIFYING AND DETECTION OF HEPATITIS B VIRAL DNA

This application is a continuation of U.S. patent application Ser. No. 08/422/018, filed Apr. 12, 1995, now abandoned, which is a continuation of U.S. patent application Ser. No. 08/090,755, filed Jul. 13, 1993, which is now abandoned.

TECHNICAL FIELD

This invention relates generally to hepatitis B virus and a method and test kit for the detection of hepatitis B virus. More particularly, the invention relates to nucleotide sequences complementary to segments of the hepatitis B virus genome which can be amplified and/or used to determine the presence of hepatitis B virus DNA in a test sample.

BACKGROUND OF THE INVENTION

The detection of viral multiplication in hepatitis B virus (hereinafter "HBV") has been found to be a useful marker of virus replication and of a patient's infectivity. HBV is the prototype agent for a new virus family called Hepadnaviridae. These viruses have small circular DNA molecules that are partly single stranded and an endogenous DNA polymerase that repairs the DNA to make it fully double stranded. A strong tropism for hepatocytes and the development of persistent infection further characterizes the group.

The complete virion of hepatitis B consists of a complex double-layered structure with an overall diameter of 42 nm. An electron dense core of 27 nm contains a circular double-stranded DNA with a molecular weight of $1.6 \times 10^6$. A 7-nm thick outer envelope surrounding the core comprises a biochemically heterogeneous complex designated HBsAg. HBsAg is produced in excess by infected hepatocytes and is released into the blood as spherical particles with a size range of 17 to 25 nm and as tubular filaments with similar diameters but various lengths. Antibodies to the core and surface antigen are designated anti-HBc and anti-HBs, respectively. A third antigen-antibody system has also been observed in hepatitis B infection and is designated HBeAg/anti-HBe. Current data suggest HBeAg is an integral part of the capsid of the hepatitis B virion. Because of its close relationship with the nucleocapsid of HBV, it is a reliable marker of virion concentration and thus for infectivity of the serum.

The goal for all current therapies for chronic type B hepatitis is the sustained inhibition of viral replication. Thus, direct reliable measure of vital DNA is very helpful for early differentiation between those patients who do and do not respond to therapy. Serum HBV-DNA and HBeAg are considered reliable markers for monitoring HBV replication.

There are four principal antigenic determinants or subtypes of HBsAg, termed adw adr, ayw, and ayr. The adw and ayr subtypes predominate in most parts of the world except in Southeast Asia and the Far East, where adr is also common. The ayr subtype is rarely observed. The group-reactive determinant a is cross-reactive among all four types, and antibody to this determinant protects against re-infection by a second subtype.

Several tests have been employed to detect HBV in serum and other body fluids. Immunological tests depend on antibodies produced in humans or animals to detect the specific viral proteins described above. However, immunological tests are indirect and may result in false positive determinations due to nonspecific antigen-antibody reactions. Furthermore, under certain circumstances the antigen-antibody tests are negative in donor serum, but the recipient of the transfused blood develops HBV infection.

Hybridization techniques such as the Southern blot or Dot Blot procedures have also been used. Generally, such techniques involve extracting DNA from cell scrapes or biopsy materials and immobilizing it on a solid phase either directly as total DNA or as restriction fragments after resolution by gel electrophoresis. The immobilized DNA is detected most commonly by a nucleic acid probe carrying a radioactive label. However, the sensitivity of standard hybridization methods is not sufficient to recognize a minimal virus replication and can therefore not distinguish infectious from non-infectious patients. To overcome this problem of sensitivity, viral DNA sequences can be amplified by using, for example, the polymerase chain reaction (PCR). The products thus obtained can be identified by using conventional hybridization techniques for identification of virus types, such as Southern blotting. See C. Oste, *BioTechniques* 6:163 (1988) and K. B. Mullis, U.S. Pat. No. 4,683,202. PCR is described in U.S. Pat. Nos. 4,683,195 and 4,683,202 and has been utilized to improve the sensitivity of standard hybridization methods. U.S. Pat. No. 4,562,159 discloses a method and kit which use PCR to specifically detect HBV DNA in a test sample. In practice, the level of sensitivity is about 50 to 100 copies per sample.

Despite these above-named screening methods, a significant percentage of post-transfusion hepatitis cases are still caused by transfusion of blood that is contaminated with HBV which eluded detection. Therefore, a need exists for an alternative method to identify HBV in clinical specimens which is more accurate, reliable and capable of semi-automation.

An alternate mechanism for target amplification is known as ligase chain reaction (LCR™) as described in EP-A-320 308 or in EP-A-439 182 LCR™ can be used to detect single or double stranded DNA targets. In this procedure, two probes (for example, A and B) complementary to adjacent regions of a target nucleic acid sequence are hybridized and ligated by DNA ligase. This ligated probe then is denatured away from the target, after which it is hybridized with two additional probes (A' and B') of sense opposite to the initial probes A and B. The secondary probes are themselves then ligated. Subsequent cycles of denaturation/hybridization/ligation create the formation of double-length probes of both sense (+) and antisense (−). By repeated cycles of hybridization and ligation, amplification of the target nucleic acid sequence is achieved.

Up to now, LCR has not been used in the detection and/or quantitation of HBV. It therefore would be advantageous to provide oligonucleotide strands of DNA which could be amplified and used to detect the presence, if any, of HBV in a test sample by using LCR. The combined use of oligonucleotide strands would be advantageous for allowing for the specific and sensitive in vitro diagnosis of the presence and specific type of HBV present in test samples. It also would be advantageous to provide a method which provides a degree of quantitation of HBV in a test sample to monitor the success of drug therapy of patients with chronic active hepatitis.

SUMMARY OF THE INVENTION

Oligonucleotide probes of from about 10 to about 60 nucleotides having a nucleotide sequence hybridizable under hybridizing conditions to a target nucleic acid sequence of hepatitis B virus are provided. The target HBV sequences (SEQ ID Nos. 21, 22, 23, 24 and 25) and the oligonucleotide probes may be selected from at least one of the following:

In one embodiment, the ligation incompetent end is corrected by extension of the 3' end of the upstream probe with nucleotides complementary to the intervening unhybridized portion of the target nucleic acid sequence so that

| SEQ ID No | |
|---|---|
| 21 | Target Sequence at Position 184-226 |
| | 5'-pGACCCCTGCTCGTGTTACAGGCGGGGTTTTTCTTGTTGACAA-3' |
| | 3'- CTGGGGACGAGCACAATGTCCGCCCCAAAAAGAACAACTGTTp-5' |
| 5 | 5'- GACCCCTGCTCGTGTTACAGG |
| 7 | pGGGGTTTTTCTTGTTGACAA-3' |
| 6 | 3'- CTGGGGACGAGCACAATGTC |
| 8 | 3'-GCCCCAAAAAGAACAACTGTT-5' |
| 22 | Target Sequence at Position 231-251 |
| | 5'-CCTCACAATACCGCAGAGTCTAGACTCGTGGTGGACTTCTCTCAATTTTCT-3' |
| | 3'-TTAGGAGTGTTATGGCGTCTCAGATCTGAGCACCACCTGAAGAGAGTTAAAAGp-5' |
| 9 | 5'-CCTCACAATACCGCAGAGTCTAGA |
| 11 | pGTGGTGGACTTCTCTCAATTTTCT-3' |
| 32 | xATCGTGGTGGACTTCTCTCAATTTTCT-3' |
| 10 | 3'-TTAGGAGTGTTATGGCGTCTCAGAp' |
| 31 | 3'-TTAGGAGTGTTATGGCGTCTCAGATCAx; |
| 12 | GAGCACCACCTGAAGAGAGTTAAAAG-5' |
| 33 | GAGCACCACCTGAAGAGAGTTAAAA-5' |
| 23 | Target Sequence at Position 403-450 |
| | 5'-pTTCCTCTTCATCCTGCTGCTATGCCTCATCTTCTTGTTGGTTCTTCTG-3' |
| | 3' -AAGGAGAAGTAGGACGACGATACGGAGTAGAAGAATAACCAAGAAGAC-5' |
| 1 | 5'- TTCCTCTTCATCCTGCTGCTATG |
| 3 | pCTCATCTTCTTGTTGGTTCTTCTG-3' |
| 28 | xACTCATCTTCTTGTTGGTTCTTCTG-3' |
| 2 | 3'- AAGGAGAAGTAGGACGACGATAp |
| 27 | 3'- AAGGAGAAGTAGGACGACGATAAx |
| 4 | GGAGTAGAAGAACAACCAAGAAGAC-5' |
| 24 | Target Sequence at Position 664-711 |
| | 5'- pCTCTTGGCTCAGTTTACTAGTGCCATTTGTTCAGTGGTTCGTAGGG-3' |
| | 3'- AAGAGAACCGAGTCAAATGATCACGGTAAACAAGTCACCAAGCATCp-5' |
| 17 | 5'-    CTCTTGGCTCAGTTTACTAGTG |
| 19 | pTTTGTTCAGTGGTTCGTAGGG-3' |
| 36 | xACATTTGTTCAGTGGTTCGTAG    -3' |
| 18 | 3'- AAGAGAACCGAGTCAAATGATp |
| 35 | 3'-    GAGAACCGAGTCAAATGATCACTx |
| 20 | GGTAAACAAGTCACCAAGCATC- 5' |
| 37 | GTAAACAAGTCACCAAGCATC- 5' |
| 25 | Target Sequence at Position 1875-1894 |
| | 5'-pCAAGCTGTGCCTTGGGTGGCTTTGGGGCATGGACATTGACCCTTATAAAG-3' |
| | 3'- GTTCGACACGGAACCCACCGAAACCCCGTACCTGTAACTGGGAATATTTC-5' |
| 13 | 5'- CAAGCTGTGCCTTGGGTGGCTTT |
| 15 | pGCATGGACATTGACCCTTATAAAG-3' |
| 14 | 3'- GTTCGACACGGAACCCACCGp |
| 16 | CCCCGTACCTGTAACTGGGAATATTTC-5' | x is hydroxyl unless otherwise specified.
Underlines bases are deliberate mismatches, as described herein.

x is hydroxyl unless otherwise specified. Underlined bases are deliberate mismatches, as described herein.

Single oligonucleotide probes are selected from the following group: SEQ ID No. 1, 3, 5, 7, 9, 11, 13, 15, 17, and 19 or their complements.

Also provided is a composition for detecting hepatitis B virus DNA present in a test sample containing non-target DNA in which the composition comprises a first upstream oligonucleotide probe and a first downstream oligonucleotide probe, each probe comprising from about 10 to about 60 nucleotides hybridizable under hybridizing conditions to the same strand of a target nucleic acid sequence of hepatitis B virus, the 3' end of the upstream probe being hybridized proximate to the 5' end of the downstream probe, and wherein the target nucleic acid sequence is at least one sequence selected from the group consisting of SEQ Id Nos. 21, 22, 23, 24, and 25 as described above or their complements. The composition is further described as having the 3' end of the upstream probe and the 5' end of the downstream probe ligation incompetent absent corrections of the ends.

the ends are ligation competent. Such compositions may be selected from the following pair sets or their complements:

| | SEQ ID No | | |
|---|---|---|---|
| Pair Set | Target HBV Sequence | Upstream Probe | Downstream Probe |
| 1 | 23 | 1 | 3 |
| 2 | 21 | 5 | 7 |
| 3 | 22 | 9 | 11 |
| 4 | 25 | 13 | 15 |
| 5 | 24 | 17 | 19 |

In another embodiment of the present invention, the ligation-incompetent ends are corrected by removal of a non-phosphorylated or mismatched base from the terminus of the 5' end of the downstream probe by a target-dependent exonucleolytic agent, followed by extension of the corresponding upstream probe with nucleotides complementary to the intervening unhybridized portion of the target nucleic acid sequence so that the ends are ligation competent. Such compositions may be selected from the following pair sets or their complements:

| | SEQ ID No | | |
|---|---|---|---|
| Pair Set | Target HBV Sequence | Upstream Probe | Downstream Probe |
| 6 | 23 | 1 | 28 |
| 7 | 22 | 9 | 32 |
| 8 | 24 | 17 | 36 |

In a third embodiment of the invention, the downstream probe forms a 5' overhang when hybridized to its target, and the correction comprises removal of the overhang such that the 5' end of the corrected downstream probes abuts the 3' end of the upstream, so that the ends of the probes are ligation competent.

Further provided is a composition for detecting the DNA of hepatitis B virus present in a test sample, said composition comprising a first and second oligonucleotide probe of from about 10 to about 60 nucleotides capable of hybridizing to a target nucleic acid sequence of hepatitis B virus, wherein the target nucleic acid sequence is selected from at least one sequence selected from the group consisting of SEQ Id Nos. 21, 22, 23, 24, and 25 as described above or their complements, and wherein the probes are hybridizable to opposite strands at opposite ends of the same target nucleic acid sequence of hepatitis B virus DNA. The pairs may be selected from the following pair sets or their complements:

| | SEQ ID No | | |
|---|---|---|---|
| Pair Set | Target HBV Sequence | First Upstream Probe | Second Upstream Probe |
| 9 | 23 | 1 | 4 |
| 10 | 21 | 5 | 8 |
| 11 | 22 | 9 | 12 |
| 12 | 25 | 13 | 16 |
| 13 | 24 | 17 | 20 |

Also provided is a composition for detecting the DNA of hepatitis B virus present in a test sample, the composition defined as:

(a) a first set of oligonucleotides comprising a first upstream probe and a first downstream probe, each probe comprising from about 10 to about 60 nucleotides hybridizable under hybridizing conditions to the same strand of a target nucleic acid sequence of hepatitis B virus, the 3' end of the first upstream probe being hybridized proximate to the 5' end of the first downstream probe; and wherein the target nucleic acid sequence is at least one sequence selected from the group consisting of SEQ Id Nos. 21, 22, 23, 24, and 25 as described above or their complements; and (b) a second set of oligonucleotides comprising a second upstream probe and a second downstream probe; both probes hybridizable to the first set of oligonucleotides of step (a), the 5' end of the second upstream probe being hybridized proximate to the 3' end of the second downstream probe. The composition has ligation incompetent ends which are corrected by extension of the 3' end of the first upstream probe with nucleotides complementary to the intervening unhybridized portion of the target nucleic acid sequence so that the ends are ligation competent.

In one embodiment, the four oligonucleotide probes are selected from the group consisting of:

(a) Set 403G, wherein SEQ Id Nos. 1 and 3 are the first upstream and first downstream probes, respectively and SEQ Id Nos 2 and 4 are the second downstream and second upstream probes, respectively;

(b) Set 184G, wherein SEQ Id Nos. 5 and 7 are the first upstream and first downstream probes, respectively and SEQ Id Nos 6 and 8 are the second downstream and second upstream probes, respectively;

(c) Set 231G, wherein SEQ Id Nos. 9 and 11 are the first upstream and first downstream probes, respectively and SEQ Id Nos 10 and 12 are the second downstream and second upstream probes, respectively;

(d) Set 1875G, wherein SEQ Id Nos. 13 and 15 are the first upstream and first downstream probes, respectively and SEQ Id Nos 14 and 16 are the second downstream and second upstream probes, respectively; and (e) Set 664G, wherein SEQ Id Nos. 17 and 19 are the first upstream and first downstream probes, respectively and SEQ Id Nos 18 and 20 are the second downstream and second upstream probes, respectively. These sets are exemplified as:

| | SEQ ID No. | | |
|---|---|---|---|
| LCR Set: | Target HBV Sequence | First Upstream, Downstream Probes | Second Downstream, Upstream Probes |
| 403G | 23 | 1,3 | 2,4 |
| 184G | 21 | 5,7 | 6,8 |
| 231G | 22 | 9,11 | 10,12 |
| 1875G | 25 | 13,15 | 14,16 |
| 664G | 24 | 17,19 | 18,20 |

In another embodiment, the composition has ligation-incompetent ends which are corrected by removal of a non-phosphorylated or mismatched base from the terminus of the 5' end of the first downstream probe by a target-dependent exonucleolytic agent, followed by extension of the upstream probe with nucleotides complementary to the intervening unhybridized portion of the target nucleic acid sequence so that the ends are ligation competent.

The composition has four oligonucleotide probes are selected from the group consisting of:

(a) Set 403E, wherein SEQ Id Nos. 1 and 28 are the first upstream and first downstream probes, respectively and SEQ Id Nos 27 and 4 are the second downstream and second upstream probes, respectively;

(b) Set 231E (SEQ Id Nos. 9, 31, 32, and 33; wherein SEQ Id Nos. 9 and 32 are the first upstream and first downstream probes, respectively and SEQ Id Nos 31 and 33 are the second downstream and second upstream, respectively; and (c) Set 664E wherein SEQ Id Nos. 17 and 36 are the first upstream and first downstream probes, respectively and SEQ Id Nos 35 and 37 are the second upstream and second downstream probes, respectively. These sets are exemplified as follows:

| LCR Set: | Target HBV Sequence | First Upstream, Downstream Probes | Second Downstream, Upstream Probes |
|---|---|---|---|
| 403E | 23 | 1,28 | 27,4 |
| 231E | 22 | 9,32 | 31,33 |
| 664E | 24 | 17,36 | 35,37 |

In another embodiment, the composition comprises a downstream probe having a 5' overhang when hybridized to its target, and the correction comprises removal of the overhang such that the 5' end of the corrected downstream probes abuts the 3' end of the upstream, so that the ends of the probes are ligation competent.

Further provided is a method for determining the presence of hepatitis B virus DNA in a test sample wherein the target sequence is selected from at least one sequence selected from the group consisting of SEQ Id Nos. 21, 22, 23, 24, and 25 and their complements, comprising hybridizing the DNA in the test sample with at least one oligonucleotide probe of the present invention wherein the hybridized probe is capable of differentiation from the unhybridized probe, and detecting the presence of the hybridized probe.

In another embodiment, ligatable pair sets are utilized in a method for determining the presence of hepatitis B virus DNA in a test sample wherein the target sequence is selected from at least one sequence selected from the group consisting of SEQ Id Nos. 21, 22, 23, 24, and 25 and their complements, comprising: (a) hybridizing the DNA in the test sample with at least one an upstream oligonucleotide probe and at least one downstream oligonucleotide probe according to the present invention, to the same strand of a target nucleic acid sequence of hepatitis B virus, said hybridization resulting in ligation-incompetent ends, absent correction; (b) correcting the 3' end of the upstream probe in a target dependent manner to render the probes ligatable; (c) ligating the 3' end of the hybridized upstream probe to the 5' end of the hybridized downstream oligonucleotide probe, wherein the hybridized probe is capable of differentiation from the unhybridized probe; and (d) detecting the presence of the hybridized probe.

A still further embodiment is a method for determining the presence of hepatitis B virus DNA in a test sample by PCR wherein the target sequence is selected from at least one sequence selected from the group consisting of SEQ Id Nos. 21, 22, 23, 24, and 25 and their complements, comprising: (a) hybridizing the first oligonucleotide probe and the second oligonucleotide probe to opposite strands at opposite ends of the same target nucleic acid sequence of hepatitis B virus DNA; (b) extending the hybridized first and second oligonucleotide probes to be contiguously complementary to the target sequence, wherein the hybridized probes are capable of differentiation from the unhybridized probes; and (c) detecting the presence of the hybridized probes.

LCR pairs are also used in a method of detecting the presence, absence or quantity of hepatitis B virus DNA in a test sample wherein the target sequence is selected from at least one sequence selected from the group consisting of SEQ Id Nos. 21, 22, 23, 24, and 25 and their complements comprising the steps of:

(a) exposing a sample suspected of containing the single stranded target nucleic acid sequence to a first set of oligonucleotides comprising a first upstream probe and a first downstream probe; each probe hybridizable under said hybridizing conditions to the same strand of said target nucleic acid sequence of hepatitis B virus, wherein the 5' end of the downstream probe and/or the 3' end of the probe is ligation incompetent absent correction to permit hybridization of said probes to target;

(b) correcting the 3' end of the first upstream probe and the 5' end of the first downstream probe only when said probes are hybridized to the target sequence, whereby the correction renders the ends ligation competent;

(c) ligating the first two probes to form a first ligated product and separating said first ligated product from the target;

(d) exposing the mixture under hybridizing conditions to a second set of oligonucleotides comprising a second upstream probe and a second downstream probe, and ligating the second two second probes to form a second ligated product, separating the second ligated product from the first ligated product, and wherein the ligated probes are capable of differentiation from the unligated probes; and repeating steps (a) through (c) at least once; and (e) determining the presence of the ligated oligonucleotide probes, said presence being related to the presence, absence or quantity of the target DNA.

A kit for detecting hepatitis B virus comprising at least one oligonucleotide according to the present invention targeted to at least one sequence selected from the group consisting of SEQ Id Nos. 21, 22, 23, 24, and 25 and their complements, said oligonucleotide being labeled so as to be capable of detection; and means for detecting said oligonucleotide and further comprises reagents for amplifying sample hepatitis B virus DNA.

DETAILED DESCRIPTION OF THE INVENTION

Definitions

Figure 1:
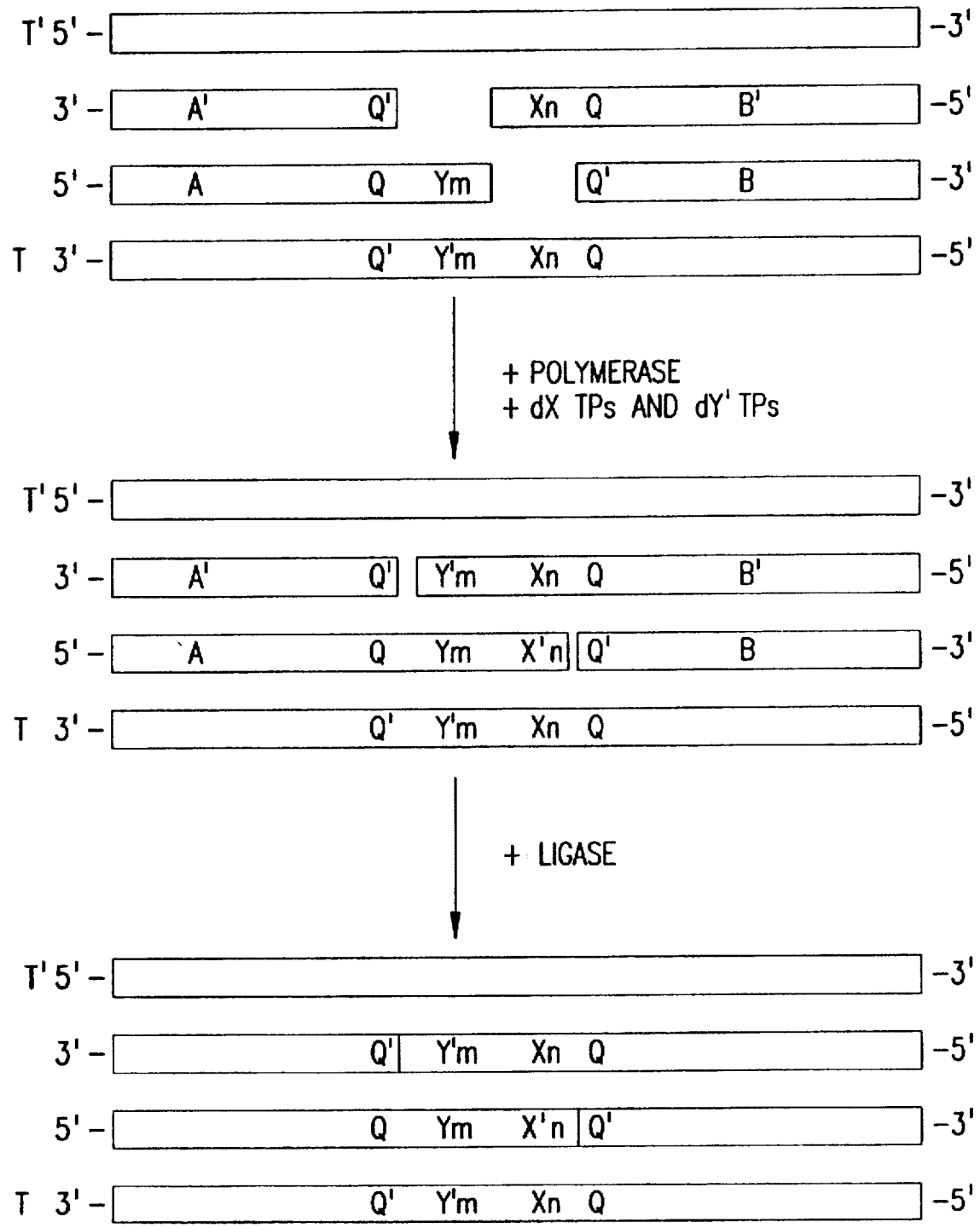
FIG. 1 is a graphic representation of the process of ligase chain reaction as it is known in the prior art.

For the purposes of the present invention, the following terms are defined.

"Assay Conditions" refers to the conditions of LCR with regard to temperature, ionic strength, probe concentration and the like. These are generally known in the art. LCR involves essentially two states or conditions: annealing or hybridization conditions, and denaturation conditions.

"Hybridization conditions" is defined generally as conditions which promote annealing and hybridization. It is well known in the art, however, that such annealing and hybridization is dependent in a rather predictable manner on several parameters, including temperature, ionic strength, probe length and G:C content of the probes. For example, lowering the temperature of the reaction promotes annealing. For any given set of probes, melt temperature, or Tm, can be estimated by any of several known methods. Typically assay conditions include temperatures which are slightly below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased probe length are also known to stabilize duplex formation because G:C pairings involve 3 hydrogen bonds where A:T pairs have just two, and because longer probes have more hydrogen bonds holding the bases together. Thus a high G:C content and longer probe lengths impact the "assay conditions" by lowering the melt temperature. Once probes are selected, the G:C content and length will be known and can be accounted for in determining precisely what "assay conditions" will encompass. Since ionic strength is typically optimized for enzymatic activity, the only parameter left to vary is the temperature and obtaining suitable "assay conditions" for a particular probe set and system is well within ordinary skill.

"Denaturation conditions" is defined generally as conditions which promote dissociation of double stranded oligonucleotides to the single stranded form. These conditions include high temperature and/or low ionic strength; essentially the opposite of the parameters described above as is well understood in the art.

"Complementary" with respect to bases refers to the following base pairs in the case of DNA: A and T; C and G; in the case of RNA: A and U and C and G. Thus, G is complementary to C and vice versa. Complementary bases are "matching", non-complementary bases are "mismatched". With respect to nucleic acid sequences, a nucleic acid sequence or probe that is "complementary" to a probe or target means the sequence can hybridize to the complementary probe or target under assay conditions. Thus, they include sequences that may have mismatched base pairs in the hybridizable region, provided the sequences can be made to hybridize under assay conditions. As defined below, probe A is complementary to probe A' and probe B is complementary to probe B'.

"Correction" refers to the process of rendering, in a target dependent manner, the upstream probes ligatable to their downstream partners. Thus, only those probes hybridized to target, target complement or polynucleotide sequences generated therefrom are "corrected." Preferably, the hybridized probes are enzymatically corrected in a manner which is dependent upon the sequence information contained within the target to render them ligatable to each other. The preferred enzyme is a DNA polymerase exhibiting 5' to 3' target dependent exonuclease activity. A 5' to 3' target dependent exonuclease activity can also be used in combination with a reagent with 5' to 3' target dependent polymerase activity. "Correction" can be accomplished by several procedures, depending on the type of modified end used. For example, some of the probes of the present invention, were designed to be "corrected" by gap filling as described in U.S. Ser. No. 07/769,743 filed Oct. 1, 1991, U.S. Pat. No. 5,578,458 or by exonuclease cleavage as described in U.S. Ser. No. 07/925,402 filed Aug. 3, 1992, abandoned, both of which are herein incorporated by reference.

"Exo format" refers to correction of ligatable-incompetent ends by removal of a non-phosphorylated or mismatched base from the 5' end of a downstream oligonucleotide probe by a target-dependent exonucleolytic agent, followed by extension of the 3' end of a proximate upstream probe with nucleotides complementary to the intervening unhybridized portion of the target nucleic acid sequence so that the ends are ligation competent.

"Exonucleolytic" refers to the excising activity, preferably of an enzyme, from the 5'-end of a DNA or RNA substrate. Exonucleolytic activity may be associated with an exonuclease or the 5'-3' exonuclease activity traditionally associated with some DNA polymerases. Generally, exonucleolytic activity is template-dependent, as is discussed in more detail below.

"Gap format" refers to a method for correcting ligation incompetent ends by extending the 3' end of an upstream oligonucleotide probe hybridized to target with nucleotides complementary to the intervening unhybridized portion of the target nucleic acid sequence so that the ends are capable of ligation.

"Ligation" is a general term and refers to any method of covalently attaching two probes. Enzymatic and photo-ligation are two commonly used methods of ligation. The conditions and reagents which make possible the preferred enzymatic ligation step are generally known to those of ordinary skill in the art and are disclosed in the references mentioned in background. Ligating reagents useful in the present invention include T4 ligase, and prokaryotic ligases such as *E. coli* ligase, and *Thermus thermophilus* ligase (e.g., ATCC 27634) as taught in EP-320 308. This latter ligase is presently preferred for its ability to maintain activity during the thermal cycling of LCR™. Absent a thermally stable ligase, the ligase must be added again each time the cycle is repeated. Also useful are eukaryotic ligases, including DNA ligase of Drosophila, reported by Rabin, et al., *J. Biol. Chem.* 261:10637–10647 (1986). One alternative to enzymatic ligation is photo-ligation as described in EP-A-324 616.

"Ligation incompetent absent correction" describes the 3' end of an upstream probe or the 5' end of a downstream probe which is incapable of being ligated to another probe, absent correction in a target dependent manner. The correction can be the removal, replacement, or further modification of this end to render it ligatable. An example of a ligation incompetent end is a non-phosphorylated 5' terminus of a downstream probe, which cannot be ligated to the 3' end of the upstream probe but which can be corrected in a target dependent manner to render it ligatable. Another example is terminal or internal mismatches of the probe with respect to the terminus of the target. Once the probes hybridize to their respective target, these mismatches are corrected in a target dependent manner to allow ligation of the probes. Other examples are give in U.S. Ser. No. 07/925,402, supra.

"Proximate" is refers to the positioning of the upstream and downstream probes, as defined below, which are hybridized proximately to the same target strand so that their 3' and 5' ends are within about 1–20 nucleotides, more preferably about 1–10 nucleotides apart. Proximate may include gaps and overhanging extensions. In contrast, "adjacent" probes by definition are hybridized proximately so their respective 3' and 5' ends are 0 nucleotides apart. Proximate probes become adjacent upon correction.

"Upstream" and "downstream" probes refer to two different non-overlapping oligonucleotides hybridized to different regions of the same target nucleic acid strand, the 3' end of one oligonucleotide pointing to the 5' end of the other. The former is termed the "upstream" probe and the latter the "downstream" probe.

The "prime" (') designation is used to indicate a complementary base or sequence. Thus, probe A can be complementary, as defined above, to A' even though it may have ends not co-terminal with A'. The same is true of B and B'.

"Suitable and/or appropriate deoxynucleotide triphosphates" ("dNTP's") refer to nucleotides needed to fill gaps in proximate probes. The type and quantity of nucleotide required are dependent on the target DNA. Further discussion of gap filling is found below. Typical nucleotides involve guanine (G), cytosine (C), adenine (A) and thymine (T) when the context is that of DNA; in the case of RNA, the base uracil (U) replaces thymine. The term also includes analogs and derivatives of the bases named above such as described in 37 CFR 1.822(p)(1). Although the degenerate base inosine (I) may be employed with this invention, it is not preferred to use I within modified portions of the probes according to the invention.

Target Nucleic Acid Sequences

The oligonucleotide sequences of the present invention identify specific positions on the gene coding for the hepatitis B virus antigen. Different HBV strains having known genomic sequences were compared to the wild type HBV strain (strain adw) to find conserved regions and the conserved regions tested as consensus sequences. Oligonucleotide probes covering homologous regions are of the HBV genome are first tested which can then be amplified in a target dependent manner. In a preferred embodiment, the oligonucleotide sequences identify specific loci on the gene coding for the surface antigen ("S") of HBV. By way of illustration and not limitation, some exemplary nucleotide sequences and their corresponding positions on the gene coding for the surface antigen ("S") of HBV are set forth below:

It is a routine matter to synthesize the desired probes using conventional nucleotide phosphoramidite chemistry and the instruments available from Applied Biosystems, Inc. (Foster City, Calif.); DuPont, (Wilmington, Del.); or Milligen, (Bedford, Mass.). Phosphorylation of the 5' ends of the appropriate probes is necessary for ligation by ligase and may be accomplished by a kinase or by commercial synthesis reagents, as is known in the art or as added as a correction mechanism as discussed herein.

In general, the methods of the invention comprise repeated steps of (a) hybridizing the selected primary probes to the target HBV DNA (and, if double stranded so that target complement is present, to the target complement); (b) correcting the selected probes in a target dependent manner to render the primary probes ligatable; (c) ligating the corrected probe to its partner to form a fused or ligated product; and (d) dissociating the fused product from the target and repeating the hybridization, correction and ligation steps to amplify the desired target sequence.

Hybridization of Probes

General

Hybridization of probes to target (and optionally to target complement) is adequately explained in the prior art; e.g. EP-320 308, U.S. Pat. No. 5,185,243, and U.S. Pat. No. 4,883,750. Probe length, probe concentration and stringency of conditions all affect the degree and rate at which hybridization will occur. Preferably, the probes are sufficiently long to provide the desired specificity; i.e., to avoid being hybridizable to nontarget sequences in the sample. Typically, probes on the order of 15 to 100 bases serve this purpose. Presently preferred are probes having a length of from about 15 to about 40 bases.

Single Probes and Ligatable Pair Sets

The hybridization of single probes and pair sets, as defined herein, is effected at a temperature selected to give effective hybridization selectivity, preferably maximum hybridization selectivity for the specific length of the linked probe. Advantageously, moderate temperatures are normally employed for probes and probe pairs of the present invention. Temperatures will generally range from about 20° C. to 90° C., more usually from about 30° C. to 70° C., preferably 37° C. to 60° C.

Modified PCR

Hybridization for a modified form of PCR, herein called "short PCR" or "sPCR" primers will be as is generally known in the art. Typical conditions are given in example 11 and 12, below. Hybridizing conditions should enable the binding of probes to the single nucleic acid target strand. As is known in the art, the probes are selected so that their relative positions along a duplex sequence are such that an extension product synthesized from one probe, when the extension product is separated from its template (complement) serves as a template for the extension of the other probe to yield a replicate chain of defined length.

Ligase Chain Reaction

The hybridization of LCR™ probe sets to their targets and optionally to the target complements is adequately explained in the prior art; e.g., EP 320,308 and EP-439,182. The probes are added in approximately equimolar concentration since they are expected to react stoichiometrically. Each probe is present in a concentration ranging from about 5 nanomolar (nM) to about 90 nM; preferably from about 10 nM to about 35 nM. For a standard reaction volume of 50 µL, this is equivalent to adding from about $3 \times 10^{11}$ to about $1 \times 10^{12}$ molecules of each probe; and around $5 \times 10^{11}$ molecules per 50 µL has been a good starting point. The optimum quantity of probe used for each reaction also varies depending on the number of cycles which must be performed and, of course, the reaction volume. Probe concentrations can readily be determined by one of ordinary skill in this art to provide optimum signal for a given number of cycles.

The stringency of conditions is generally known to those in the art to be dependent on temperature, solvent and other parameters. Perhaps the most easily controlled of these parameters is temperature and thus it is generally the stringency parameter varied in the performance of LCR. Since the stringency conditions required for practicing this invention are not unlike those of ordinary LCR, further detail is deemed unnecessary, the routine practitioner being guided by the examples which follow.

Typically, reactions were performed in LCR Buffer (50 mM EPPS pH 7.8, 20 mM KCl, 30 mM $MgCl_2$, 10 mM $NH_4Cl$ and optionally 0.5 mM $NAD^+$) and optionally supplemented with acetylated BSA. Temperature cycling was achieved with a e.g. thermal cycler from Coy Laboratory Products (Ann Arbor, Mich.) or the Programmable Cycler Reactor™ (available from Ericomp, San Diego, Calif.).

Correction of probes

Oligonucleotide probes of the present invention may be corrected by a "gap-fill" format or "exo" format. Both types of correction are described below.

Correction by Gap-Fill Format

Probes which are corrected by a gap-fill method have modified ends which are created by eliminating from one or more of the probes a short sequence of bases, thereby leaving a recess or gap between the 5' end of one probe and the 3' end of the other probe when they are both hybridized to the target (or target complement, or polynucleotide generated therefrom). In order for LCR to amplify the target, the gaps between the probes must be filled in (i.e., the modification must be "corrected"). In the gap format, this can be done using a polymerase or a reverse transcriptase and an excess of deoxyribonucleotide triphosphates which are complementary to the target strand opposite the gap.

In this embodiment, the invention involves repeated steps of (a) hybridizing the probes to the target HBV (and, if double stranded so that target complement is present, to the target complement); (b) extending at least one probe to fill in at least one gap; (c) ligating the extended probe to the adjacent probe to form a fused or ligated product; and (d) dissociating the fused product from the target and repeating the hybridization, extension and ligation steps to amplify the desired target sequence.

In this version, which includes both single gap ("SG") and double gap ("DG") configurations, the "gaps" which impart the "modified ends" are "corrected" by extending one or both of the modified probes using a polymerase or a reverse transcriptase. Generally, extension of a probe hybridized to a HBV DNA target is accomplished by a DNA polymerase or a Klenow fragment as is known in the art. In the case of an RNA target, extension is accomplished by a reverse transcriptase. Exemplary reverse transcriptases include those from avian myeloblastosis virus (AMV) and Moloney murine leukemia virus (M-MuLV) generally available to those skilled in the art. Certain DNA polymerases will also recognize RNA as template under certain conditions. It is, of course, preferable to utilize extension reagents which are thermally stable and can withstand the cycling of high temperatures required for LCR. If the extension reagent is not thermally stable, it typically must be re-added at each cycle of LCR. Such thermostable polymerases presently include AmpliTaq™, (available from Cetus-Perkin Elmer), Thermus polymerase (available from Molecular Biology Resources, Inc. Milwaukee, Wis., "MBR") and recombinant or purified native polymerases from *Thermus aquaticus, Thermus thermophilus* or other species known to be thermostable.

Correction by extension in this manner requires the presence in the reaction mixture of deoxyribonucleotide triphosphates (dNTP's) complementary to the bases of the target in the gap region(s). More specifically, with reference to FIG. 1, for a gap having the sequence $X_n$, the dNTP's that must be supplied are designated dX'TP wherein X' stands for the complements of each base in the gap $X_n$. The dNTP's are commercially available from a number of sources, including Pharmacia (Piscataway, N.J.) and Bethesda Research Laboratories (Gaithersburg, Md.).

Extension must be terminated precisely at the point of ligation so that the extended probe abuts the adjacent probe and can be ligated to it. "Stopbases" are employed for this purpose. A "stopbase", designated Q', (see FIG. 1) is defined in terms of its complement, Q and is accomplished by omitting from the reaction mixture, dNTP's that are complementary to Q; i.e. by omitting dQ'TP from the reaction mixture. Thus it is seen how the bases for the gap sequence (s) must be selected from a set, N, consisting of only three of the four bases, so that the complementary three of the four dNTP's are added to the reaction mixture. When the fourth dNTP, dQ'TP, is absent from the reaction mixture extension will terminate at the desired point of ligation. It follows that Q' is the first base in the downstream probe, and the base on the target which codes for the stopbase is the first base adjacent the gap.

Extension by polymerase or transcriptase proceeds in a 5' to 3' direction. Consequently, the 3' ends of both upstream probe (FIG. 1, probes A and B') will be extendible by polymerase in the absence of anything to prevent extension. Extension is terminated when the next base called for by the template is absent from the reaction mixture. Thus, probe A is extended through gap $X_n$ until stopbase complement (Q) is encountered along the target strand. Similarly, probe B' is extended through gap $Y_m$ until stopbase complement (Q) is encountered (either on the target complement or on the A half of reorganized A:B). Neither probe A' nor B will serve as a template for extension of A or B', so probes A and B' are extended only if hybridized to the target (or to reorganized polynucleotide products from previous cycles).

As alluded to above, it is important to terminate the extension of A and B' at the end of the respective gaps (i.e., at the point of ligation) so that the extended probe can be ligated to the 5' end of the downstream probes, B and A'. Therefore, the reaction mixture omits the deoxyribonucleotide triphosphate complementary to the base (Q) immediately adjacent the 5' end of gaps $X_n$, and $Y_m$. Of course, it will be understood that it is not required that the same base stop extension in both directions. A different base can be used provided it is not needed to fill either of the gaps. It should now be apparent that the actual points of ligation in this embodiment are always at the 5' ends of the downstream probes (A' and B). It is not by mere coincidence that these are also the locations of the stopbases Q'.

Accordingly, the gaps $X_n$ and $Y_m$ can be any number of bases long, i.e., n can be any integer greater than or equal to 1, and m is any integer greater than 0. It is to realized, however, that the choice of which gap is $X_n$ and which is $Y_m$ is arbitrary in the first place; but n and m cannot both be zero. The gaps need not be the same length, i.e., m need not equal n. When, m equals zero, the double gap variation degenerates into the specialized case of the single gap, which is not used in the embodiment being claimed herein. The only restriction on the bases X is that they be selected from a set N which consists of from 1 to any 3 of the four bases. Similarly, the bases Y are drawn from set M. Since at least one stopbase Q' must be maintained, the combined sets N and M which represent the possible bases for X and Y, respectively, must include no more than three of the four bases. Accordingly, Y can be from zero to any three of the four bases provided that at least one base remains in the set "not N and not M". If set N constitutes less than three of the four bases, then Y can be a base that is not within N so long as there is at least one base remaining, the complement of which can serve as the stopbase Q' for termination of probe extension. A single stopbase can serve to terminate extension in both the $X_n$ and $Y_m$ gaps.

A second limitation on sequence $Y_m$ occurs if m equals n. If the gaps are the same length, the sequence $Y_m$ should not be complementary to the sequence $X_n$ or the 3' ends of probes A and B' would constitute "sticky ends". "Sticky ends" would permit a target independent double stranded complex to form wherein probe A hybridizes to probe B' such that ligations and amplification would proceed. Rather, when m equals n it is preferred that $Y_m$ not be complementary to $X_n$. In other words, the ends of probes A and B' should at least be "slippery ends" which may be the same length, but are not complementary.

In a preferred aspect of the invention, the fourth probe B' includes a 3' terminal sequence of $X_n$, identical in length to the $X_n$ sequence gap in the target. This arrangement is not essential to the invention, however, as the gap need only be formed between the probes. Thus, the 3' terminus of the fourth probe B' may stop short of the 3' end of sequence $X_n$, provided there is no 3' recessed end with respect to the second probe B. Since extension occurs in a 5' to 3' direction and dXTPs must be present anyway (to extend through $X_n$), probe B' would be extended through the gap, (both $Y_m$ and any remainder of $X_n$) just as the first probe A is extended through the $X_n$ gap.

Correction by the "Exo Format"

In this embodiment, a ligation incompetent end may be a nonphosphorylated 5' terminus of a downstream probe, which cannot be ligated to the 3' end of the upstream probe but which can be corrected in a target dependent manner to render it ligatable. Another example of a ligation incompetent end may be terminal or internal mismatches of the probe with respect to the terminus of the target. Once these types of probes hybridize to their respective target, these mismatches are corrected in a target dependent manner by modification of the 5' end of one or more of the probes by eliminating a short sequence of bases, thereby leaving a recess or gap between the 5' end of one probe and the 3' end of the other probe when they are both hybridized to the target (or target complement, or polynucleotide generated therefrom). This modification is corrected by an exonucleolytic activity, preferably the 5' to 3' exonuclease activity associated with a DNA polymerase (Gelfand, D., *Taq DNA Polymerase in PCR Technology: Principles and Applications for DNA Amplification*, Erlich, H. A., Ed., Stockton Press, New York (1989)). In the presence of the appropriate deoxynucleotides, these DNA polymerases will initiate synthesis from the 3' hydroxyl end of a probe hybridized to a target DNA, proceed along the DNA target template, hydrolyzing hybridized DNA sequences and replacing them in the process. The exonucleolytic degradation of the DNA sequences results in the release of mono, di, and larger nucleotide fragments. Typically this exonuclease activity is synthesis dependent. It therefore follows that the termination of synthesis should result in the termination of 5' to 3' exonuclease activity. One way to terminate synthesis in a controlled manner is to limit the dNTP pool by leaving out one or several of the four dNTPs required for DNA synthesis. Synthesis by DNA polymerase will continue until a template base ("stop base") on the target is encountered which is complementary to a deoxyribonucleoside 5'-triphosphate omitted from the dNTP pool. The degradation and synthesis would then terminate at this point.

In LCR, a downstream probe containing a 5' end which is ligation incompetent absent correction is used. The modification prevents the target independent ligation of the probes. Additionally, in the presence of a target nucleic acid sequence, adjacent LCR probes would hybridize but would not be ligatable. Sequence information contained within the target DNA is used as a template for correction of the ligation incompetent end. A DNA polymerase with synthesis dependent, strand replacement 5' to 3' exonuclease activity is used to extend the upstream probe and hydrolyze the downstream probe using the target nucleic acid as a template. By using a subset of four dNTPs required for DNA synthesis, the extension of the upstream probe and thereby the hydrolysis of the downstream probe could be controlled such that when a template base in the target is encountered to which no complementary dNTP is present, synthesis and hydrolysis would stop. The resultant downstream probe would terminate with a 5' phosphate which would be adjacent to the 3' hydroxyl end of the extended upstream probe. Adjacent DNA sequences in this orientation represent a suitable substrate for ligation by DNA ligase.

The resulting gap between the probes must be filled in (i.e., the modification must be "corrected"). This correction proceeds as described above for the gap-filling format.

Ligation

Following correction, the next step in the general method comprises the ligation of one probe to its adjacent partner. Thus, each corrected first upstream (or primary) probe is ligated to its associated first downstream probe and each corrected second downstream (or secondary) probe is ligated to its associated secondary upstream probe. An "adjacent" probe is either one of two probes hybridizable with the target in a contiguous orientation, one of which lies with its phosphorylated 5' end in abutment with the 3' hydroxyl end of the partner probe. "Adjacent" probes are created upon correction of the modified end(s) in a target dependent manner, as described above. Enzymatic ligation is the preferred method of covalently attaching two adjacent probes; however, "ligation" is a general term and is to be understood to include any method of covalently attaching two probes.

The conditions and reagents which make possible the preferred enzymatic ligation step are generally known to those of ordinary skill in the art and are disclosed in the references mentioned in background. Ligating reagents useful in the present invention include T4 ligase, and prokaryotic ligases such as *E coli* ligase, and *Thermus thermophilus* ligase (e.g., ATCC 27634) as taught in EP-320 308. This latter ligase is presently preferred for its ability to maintain activity during the thermal cycling of LCR. Absent a thermally stable ligase, the ligase must be added again each time the cycle is repeated. Also useful are eukaryotic ligases, including DNA ligase of Drosophila, reported by Rabin, et al., *J. Biol. Chem.* 261:10637–10647 (1986).

Once ligated, the fused, reorganized probe is dissociated (e.g. melted) from the target and, as with conventional LCR, the process is repeated for several cycles. The number of repeat cycles may vary from 1 to about 100, although from about 15 to about 70 are preferred presently.

It is desirable to design probes so that when hybridized to their complementary (secondary) probes, the ends away from the point of intended ligation are not able themselves to participate in other unwanted ligation reactions. Thus, ligatable sticky or blunt ends should be avoided. If such ends must be used, then 5' terminal phosphates should be avoided, eliminated or blocked. This can be accomplished either through synthesizing oligonucleotide probes (which normally carry no 5' terminal phosphate groups), or through the use of phosphatase enzymes to remove terminal phosphates (e.g. from oligonucleotides generated through restriction digests of DNA). Alternatively, ligation of the "wrong" outside ends of the probes can be prevented by blocking the end of at least one of the probes with a "hook" or marker moiety as will be described in detail below. In the absence of one of the above techniques, the outside ends of the probes can be staggered so that if they are joined, they will not serve as template for exponential amplification.

In a particularly preferred configuration, haptens, or "hooks", are attached at the available outside ends of at least two probes (opposite ends of fused product), and preferably to the outside ends of all four probes. A "hook" is any moiety having a specific ligand-receptor affinity. It may be for example a hapten or a segment of a polynucleotide. A hood may be attached to one probe and a label may be attached to the other probe of the same sense. Ligation joins the label to the affinity moiety and separated label can be measured on a solid phase following separation.

Detection

The presence of amplified target can be detected by any number of methods. One method is to differentiate reaction products of a specific size by means of molecular weight. Methods for molecular weight differentiation include affinity labeling, composition, gel filtration, sedimentation velocity, osmotic pressure, or gel electrophoresis. A particularly preferred method is gel electrophoresis which is particularly useful when the nucleotides used are labeled with a radiolabel, such as $^{32}$P. Typically, detection is performed after separation, by determining the amount of label in the separated fraction. Of course, label in the separated fraction can also be determined subtractively by knowing the total amount of label added to the system and measuring the amount present in the unseparated fraction. Separation may be accomplished by electrophoresis, by chromatography or by the preferred method described below. Typically, detection is performed after separation, by determining the amount of label in the separated fraction. Of course, label in the separated fraction can also be determined subtractively by knowing the total amount of label added to the system and measuring the amount present in the unseparated fraction. Where used, separation may be accomplished by electrophoresis, by chromatogaphy or by the preferred method described below.

Other methods include the use of labeling the nucleotides with a physical label which is capable of generating a detectable signal. The various "signal generating compounds" (labels) contemplated include chromogens, catalysts such as enzymes, luminescent compounds such as fluoroscein and rhodamine, chemiluminescent compounds, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Many different haptens are known, and virtually any hapten can be used with the present invention. The invention requires only that a specific binding partner is known or can be prepared (a definitional property of "hapten") and that the hapten can be coupled to the probe such that it does not interfere with hybridization. Many methods of adding haptens to probes are known in the literature. Enzo Biochemical (New York) and Clontech (Palo Alto) both have described and commercialized probe labeling techniques. For example, a primary amine can be attached to a 3' oligo end using 3'-amine-ON CPG™ (Clontech, Palo Alto, Calif.). Similarly, a primary amine can be attached to a 5' oligo end using Aminomodifier II® (Clontech). The amines can be reacted to various haptens using conventional activation and linking chemistries.

In addition, copending applications U.S. Ser. No. 07/625,566, filed Dec. 11, 1990, abandoned and Ser. No. 07/630,908, filed Dec. 20, 1990, U.S. Pat. No. 5,290,925 teach methods for labeling probes at their 5' and 3' ends respectively. Both the aforementioned copending applications are incorporated by reference. Some illustrative haptens include many drugs (e.g. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-pending, co-owned patent applications U.S. Ser. No. 07/808,508 (adamantaneacetic acid), abandoned, 07/808,839 (carbazole and dibenzofuran), abandoned, both filed Dec. 17, 1991, U.S. Ser. No. 07/858,929, abandoned, and U.S. Ser. No. 07/858,820, abandoned, both filed Mar. 27, 1992 (collectively referred to herein as the "hapten applications"). The entire disclosure of each of the above hapten applications is incorporated herein by reference.

Protocols for the detection of more than one target, for example HBV and HCV, may include two labels, a common label and a unique label as more fully described in U.S. Ser. No. 07/860,702 filed Mar. 31, 1992, abandoned. Either may serve as the detection label. For simplicity, the embodiments are described using haptens as both the common and unique labels. It is, of course, understood that another label is easily substituted for at least one of the haptens, especially the common hapten.

According to a preferred standard LCR protocol, a first hapten is used to capture and separate the reorganized molecules. A second hapten is used to couple the reorganized complex with the signaling entity. This procedure is described more completely in EP-A-439 182. For example a fluorescein moiety is attached to the 5' end of the first primary probe and to the 3' end of the first secondary probe. In addition, a different hapten, say biotin, is attached to the 3' end of the second primary probe and to the 5' end of the second secondary probe. Thus, when the reorganized molecules are duplexed, two biotins are found at one end of the duplex and two fluoresceins are found at the other end. A solid phase having a coating of anti-fluorescein is used to separate reorganized molecules from unligated probes having biotins. (Unligated probes having fluoresceins are also captured.) The separated complexes are detected by using avidin or anti-biotin labeled with a detectable signaling entity such as an enzyme.

The test sample can be any biological material suspected of containing HBV. Thus, the test sample can be human body tissue, or a test sample which contains cells suspected of containing HBV. The term can refers to virtually any liquid sample. The test sample can be derived from any desired source, such as a physiological fluid, for example, blood, saliva, ocular lens fluid, cerebral spinal fluid, sweat, urine, milk, ascites fluid, mucous, synovial fluid, peritoneal fluid, amniotic fluid or the like. The liquid test sample can be pretreated prior to use, such as preparing plasma from blood, diluting viscous liquids, etc. Methods of pretreatment can also involve separation, filtration, distillation, concentration, inactivation of interfering components, and the addition of reagents. Besides physiological fluids, other liquid samples such as water, food products and the like can be used. In addition, a solid test sample can be used once it is modified to form a liquid medium.

Kits

Reagents employed in methods of the invention can be packaged into diagnostic kits. Diagnostic kits may include the labeled oligonucleotides; if the oligonucleotide is unlabeled, the specific labeling reagents may also be included in the kit. The kit may further contain suitably packaged combination nucleoside triphosphates, e.g., dATP, dGTP, dCTP, or dTTP or combinations of up to three of the dNTPs, depending on the particular probe design and the gap full or sexo fill needs. The kit can further include a polynucleotide polymerase and also means for covalently attaching upstream and downstream sequences, such as a ligase. These reagents will typically be in separate containers in the kit but can be packaged in one container where reactivity and shelf life permit. The relative amounts of various agents in the kits can vary widely to provide for concentrations of reagents which optimize the reactions needed to occur during the instant invention and to optimize the sensitivity of the assay. The kits may further include a denaturation agent for denaturing the analyte, hybridization buffers, wash solutions, enzyme substrates, negative and positive controls and written instructions for carrying out the assay.

The invention will now be illustrated by examples. The examples are not intended to limit the scope of the present invention. In conjunction with the general and detailed invention above, the examples provide further understanding of the present invention and outlines some aspects of the preferred embodiment of the invention.

EXAMPLES

Materials and Methods

The following terms used in the examples are trademarks, tradenames or chemical abbreviations as specified:

BSA: bovine serum albumin

EDTA: a metal chelator, ethylenediamine tetraacetic acid

EPPS: chemical abbreviation for [N-(2-hydroxyethyl) piperazine-N-(3-propanesulfonic acid)]acid, used as a buffer.

FITC: chemical abbreviation for fluorescein isothiocyanate, a fluorescent hapten derivative.

HPLC high performance liquid chromatography

MES: chemical abbreviation for [2-(N-morpholino) ethanesulfonic acid], a buffer.

IMx®: trademark of Abbott Laboratories for an automated instrument for performing microparticle enzyme immunoassay (MEIA).

Tris a buffer comprising tris(hydroxymethyl) aminomethane

The following is a table of probes and/or primers used in the examples below. Each sequence is refered to by its "SEQ ID No." in the specific example:

TABLE A

| | |
|---|---|
| 1 | 5'-pTTCCTCTTCATCCTGCTGCTATG |
| 2 | 3'- AAGGAGAAGTAGGACGACGATAp |
| 3 | pCTCATCTTCTTGTTGGTTCTTCTG-3' |
| 4 | GGAGTAGAAGAACAACCAAGAAGACp-5' |
| 5 | 5'-pGACCCCTGCTCGTGTTACAGG |
| 6 | 3'- CTGGGGACGAGCACAATGTC |
| 7 | pGGGGTTTTTCTTGTTGACAA-3' |
| 8 | 3'-GCCCCAAAAAGAACAACTGTTp-5' |
| 9 | 5'-CCTCACAATACCGCAGAGTCTAGA |
| 10 | 3'-TTAGGAGTGTTATGGCGTCTCAGAp' |
| 11 | pGTGGTGGACTTCTCTCAATTTTCT-3' |
| 12 | GAGCACCACCTGAAGAGAGTTAAAAGp-5' |
| 13 | 5'-pCAAGCTGTGCCTTGGGTGGCTTT |
| 14 | 3'- GTTCGACACGGAACCCACCGp |
| 15 | pGCATGGACATTGACCCTTATAAAG-3' |
| 16 | CCCCGTACCTGTAACTGGGAATATTTCp-5' |
| 17 | 5'- pCTCTTGGCTCAGTTTACTAGTG |
| 18 | 3'- AAGGAACCGAGTCAAATGATp |
| 19 | pTTTGTTCAGTGGTTCGTAGGG-3' |
| 20 | GGTAAACAAGTCACCAAGCATCp- 5' |
| 27 | 3'- AAGGAGAAGTAGGACGACGATAAx |
| 28 | xACTCATCTTCTTGTTGGTTCTTCTG-3' |
| 31 | 3'-TTAGGAGTGTTATGGCGTCTCAGATCAx; |
| 32 | XATCGTGGTGGACTTCTCTCAATTTTCT-3' |
| 33 | GAGCACCACCTGAAGAGAGTTAAAAp-5' |
| 35 | 3'- GAGAACCGAGTCAAATGATCACTx |
| 36 | xACATTTGTTCAGTGGTTCGTAG -3' |
| 37 | GTAAACAAGTCACCAAGCATCp- 5' |

As a sample any kind of cells, swabs, smears, blood or tissue may be prepared by centrifugation of the respective cellular suspension in phosphate-buffered saline (PBS). Generally, the pellets are resuspended in 100 μl of 10 mM NaOH and heated for 5 to 10 minutes at 100° C. After boiling, the samples are re-centrifuged and the cellular debris removed. An aliquot of the supernatant is added to a reaction mix containing 50 mM EPPS pH 7.8, 30 mM $MgCl_2$, 20 mM KCl, 1 μM deoxynucleotide triphosphate, and $5 \times 10^{11}$ molecules of oligonucleotide probe of the present invention. The capture ligand oligonucleotide A and A' may be derivatized with carbazole and/or FITC. Probe B and B' may be derivatized with adamantane or biotin as signal moieties. Polynucleotide kinase is used for phosphorylation of the selected probes' at their 5' ends. The tube tubes containing the sample and reaction mix are overlaid with mineral oil and boiled for about 3 minutes. Afterwards the tubes are held for 1 minute at 85° C. and 50° C. for another 1 minute. *Thermus thermophilus* ligase (Abbott) and Thermus DNA polymerase (Molecular Biology Resources) are added to the reaction mixture. The tubes are then alternated between 85° C. and 50° C. either in a thermal cycler or between two water baths. Normally 30 LCR cycles are sufficient to amplify the target HBV DNA for assay. For detecting the reaction product, the mix is separated from mineral oil layer and diluted with an equal volume of distilled water. A portion of the reaction mixture is loaded into a disposable reaction cell of the IMx® analyzer. The respective reagent of the test such as sample dilution buffer, methyl umbelliferone phosphate, antibiotin alkaline phosphatase conjugate, anti-fluorescein coated particles, and the like) are also loaded on the IMx® analyzer. On completion of the MEIA within 30 minutes, the rate of alkaline phosphatase bound is derived from the reaction rate in counts/sec/sec.

Quantities of polymerase are expressed in units, defined as follows: 1 unit of enzyme is as defined by the manufacturer (Molecular Biology Resources). Units of ligase enzyme are defined herein as: 1 mg of 95% purified *Thermus thermophilus* DNA ligase has a specific activity of about $1 \times 10^8$ units. While this is not precisely standardized and may vary by as much as 20%, optimization is within the skill of the routine practitioner.

LCR™ Conditions

All reactions, unless otherwise stated, were performed in LCR Buffer (50 mM EPPS pH 7.8, 20 mM KCl, 30 mM $MgCl_2$, 10 mM $NH_4Cl$). Temperature cycling was achieved with a e.g. thermal cycler from Coy Laboratory Products (Ann Arbor, Mich.) or the Programmable Cycler Reactor® (available from Ericomp, San Diego, Calif.). Reactions were terminated by transferring aliquots into Stop Buffer (80% formamide, 20 mM EDTA, 0.05% (w:v) xylene cyanol and 0.05% bromophenol blue). The ligated and unligated products were resolved on a 16×20×0.04 cm 15% polyacrylamide gel containing 8.3M urea in 80 mM Tris, 80 mM boric acid pH 8.0, 1.0 mM EDTA. The gel was autoradiographed, the autoradiograph used as a template to excise the ligated and unligated probes and the amount of radioactivity in each band was measured by liquid scintillation counting. The percentage of radioactivity in the ligated product was calculated as a function of the total counts in each lane.

Example 1

Figure 2:
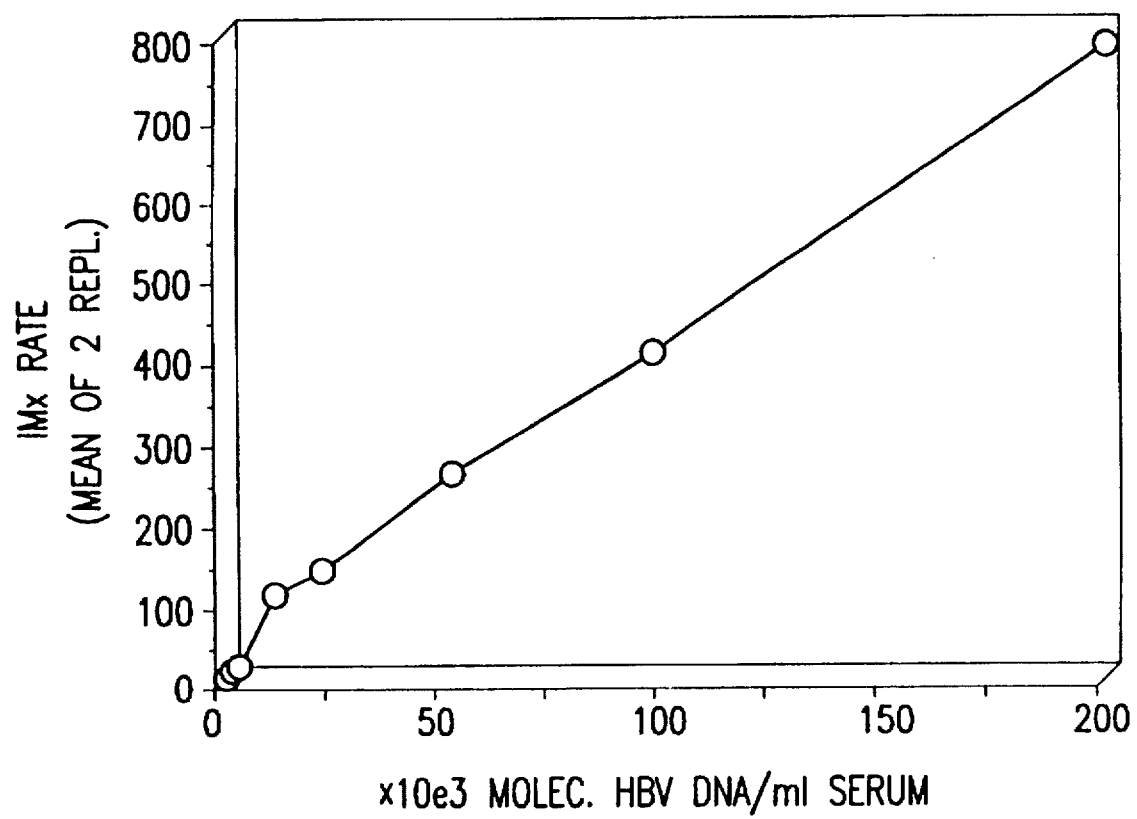
FIG. 2 is a standard curve relating the number of HBV DNA target molecules to the IMx® rate (counts/sec/sec) with probe set 403G (SEQ ID Nos. 1, 2, 3, and 4) $10^3$ HBV genome copies/mL of patient's serum. HBV DNA positive samples were diluted in human serum negative for HBV markers. The serum diluent also served as the negative control. The dilution of the positive controls indicated in the graphs as molecules of HBV DNA per mL serum, were tested in duplicates and the mean values are shown as IMx® rates. A detection limit of 5–10 fg HBV-DNA/mL sample, equivalent to about 2000–3000 genome copies/mL or 10–15 copies per assay, respectively was obtained. LCR results were obtained from Example 1, below.

LCR™ was performed using probe set 403G consisting of SEQ ID Nos. 1, 2, 3, and 4 (See Table A) in a 0.5 mL polypropylene tube containing LCR Buffer. A test sample containing HBV DNA ($2.8 \times 10^7$ molecules HBV DNA/ml) was diluted in human serum negative for HBV markers. The serum diluent also served as the negative control. Each probe was present at $5 \times 10^{11}$ molecules/reaction and the final concentration of DNA ligase at 5000 units and DNA polymerase at 1.0 units. The samples were overlaid with mineral oil and the temperature cycle consisted of a 85° C. incubation for 30 seconds followed by a 50° C. incubation for 20 seconds. The dilution of the positive controls indicated in the graphs as molecules of HBV DNA per ml serum, were tested in duplicates and the mean values are shown as IMx® rates in Table 1, below. The evaluation of the linear range is demonstrated in FIG. 2 as a linear graph. The axis values are obtained by multiplying the number of molecules/reaction (Table 1) times the number of mL in the reaction (×200)

TABLE 1

QUANTITATION OF HBV DNA IN SERUM WITH SET 403G
(SEQ ID Nos. 1, 2, 3, 4)

| Sample (Mol./react) | AVERAGE IMx® c/s/s | C.V. % Coefficient of Variation |
|---|---|---|
| Negative Control* | 4.88 | 3.9 |
| Positive Control | 1642.62 | 0.7% |
| 1000 molec. | 774.74 | 1.5% |
| 500 molec. | 407.54 | 1.5% |
| 250 molec. | 249.69 | 3.2% |
| 100 molec. | 124.05 | 6.5% |
| 50 molec. | 98.62 | 15.7% |
| 10 molec. | 15.61 | 3.1% |
| 5 molec. | 12.57 | 33.4% |
| 1 molec. | 4.70 | 16.5% |

Example 2

LCR was performed using probe set 403G (Seq Id Nos. 1, 2, 3, 4) for HBV DNA, under conditions described in Example 1, above. The results are illustrated in Table 2 below.

TABLE 2

Specificity and Sensitivity of 403G (Seq Id Nos. 1, 2, 3, 4) for HBV DNA

| NO. | NC* - REPLICATES IMx® c/s/s | 10 MOLEC REPLICATES IMx® c/s/s | 100 MOLEC REPLICATES IMx® c/s/s | 1000 MOLEC REPLICATES IMx® c/s/s |
|---|---|---|---|---|
| 1 | 6.2 | 116.9 | 638.8 | 1326.4 |
| 2 | 5.9 | 157.6 | 533.8 | 1310.0 |
| 3 | 5.8 | 179.1 | 599.1 | 1300.4 |
| 4 | 5.8 | 129.2 | 348.4 | 1337.1 |
| 5 | 5.6 | 102.6 | 616.8 | 1370.3 |
| 6 | 5.6 | | | |
| 7 | 4.9 | | | |
| 8 | 5.3 | | | |
| 9 | 5.6 | | | |
| STAT | % CV+ = 5.3 | % CV+ = 21.9 | % CV+ = 7.6 | % CV+ = 2.0 |

*NC = negative control
+% CV = Coefficient of Variation

Example 3

LCR was performed using probe sets 231E (SEQ ID Nos. 9, 31, 32, and 33) and 231G (SEQ ID Nos. 9, 10, 11, and 12) under conditions described in Example 1, above. For probe set 321E, 45 cycles were performed. The results are in Table 3, below. For probe set 231G, 40 cycles at temperature of 85° and 60° for 30 and 20 seconds, respectively, were performed. Results are shown in Table 4.

TABLE 3

Specificity And Sensitivity Of Set 231E
(SEQ ID Nos. 9, 31, 32 and 33) For HBV DNA Using LCR Exo Format

| NO. | Negative control IMx® (c/s/s) | 10 Mol. Replicates IMx® (c/s/s) | 100 Mol. Replicates IMx® (c/s/s) | 1000 Mol. Replicates IMx® (c/s/s) |
|---|---|---|---|---|
| 1 | 7.4 | 348.3 | 1101.1 | 1449.3 |
| 2 | 4.9 | 507.3 | 1049.3 | 1385.6 |
| 3 | 5.2 | 606.7 | 1086.1 | 1306.6 |
| 4 | 5.1 | | | |
| 5 | 5.3 | | | |
| 6 | 5.0 | | | |
| 7 | 5.0 | | | |
| 8 | 4.7 | | | |
| 9 | 5.7 | | | |
| 10 | 5.7 | | | |
| 11 | 5.1 | | | |
| 12 | 5.0 | | | |
| 13 | 5.2 | | | |
| 14 | 5.5 | | | |
| 15 | 6.2 | | | |
| STAT | % CV = 12.4 | % CV = 26.4 | % CV = 2.4 | % CV = 5.2 |

TABLE 4

Specificity And Sensitivity Of Set 231G
(SEQ ID Nos. 9, 10, 11, and 12) For HBV DNA Using LCR Gap Format

| No. | Negative Control* Imx c/s/s | 1000 mol. Imx c/s/s | $1.4 \times 10^5$ mol/rxn Imx c/s/s |
|---|---|---|---|
| 1 | 9.97 | 623.9 | 1289.8 |
| 2 | 9.97 | 297.8 | 1278.8 |
| 3 | 9.97 | 604.3 | 1246.8 |
| 4 | 9.97 | 449.5 | 1267.3 |
|  | % CV = 25.1 | % CV = 30.9 | % CV = 1.4 |

*data represented as mean of 40 samples

Example 4

LCR was performed using probe sets 664G (SEQ ID Nos. 17, 18, 19, and 20) and 664E (SEQ ID Nos. 17, 35, 36 and 37) under conditions described in Example 1, above. The results are illustrated in Table 5 and Table 6 for 664G and 664E, respectively.

TABLE 5

Specificity And Sensitivity Of 664G
(SEQ ID Nos. 17, 18, 19, and 20) For HBV DNA:

| NO. | NC IMx c/s/s | 1000 molec. IMx rates | 140,000 molec. IMx rates |
|---|---|---|---|
| 1 | 5.8 | 6.4 | 46.2 |
| 2 | 6.0 | 7.0 | 40.1 |
| 3 | 6.3 | 6.3 | 44.2 |
| 4 | 6.6 | 6.9 | 27.8 |
| 5 | 6.7 | 6.6 | 22.6 |
| STAT | x = 6.28 (±0.37) % CV = 5.9 | x = 6.65 (±0.30) % CV = 4.5 | x = 36.34 (±10.51) % CV = 28.9 |

TABLE 6

Specificity And Sensitivity Of 664E
(SEQ ID Nos. 17, 35, 36 and 37) For HBV DNA:

| NO. | NC IMx c/s/s | 1000 molec. IMx rates | 140,000 molec. IMx rates |
|---|---|---|---|
| 1 | 11.4 | 36.9 | 345.2 |
| 2 | 13.2 | 31.2 | 375.3 |
| 3 | 15.4 | 28.4 | 273.2 |
| STAT | x = 13.37 | x = 32.19 | x = 331.24 |
|  | (±2.01) | (±4.29) | (±52.45) |
|  | % CV = 15.1 | % CV = 13.3 | % CV = 15.8 |

Example 5

LCR was performed using probe set 403G (SEQ ID Nos. 1, 2, 3, and 4) under conditions described in Example 1, above except that 1350 units of ligase were used. The specificity of these probes for HBV-DNA was demonstrated using 31 serum samples from healthy, non B hepatitis and auto immune hepatitis patients (see Table 6, below). Each patient tested negative as indicated by liver function tests indicating no false positives using the LCR method. Each test sample had 250 molecules of HBV DNA per serum sample. Healthy patients had no liver disease, non-B hepatitis patients demonstrated positive signs of liver disease and autoimmune hepatitis patients had hepatitis-like symptoms and clinical manifestation of liver problems.

TABLE 6

Evaluation Of 31 Serum Samples Using HBV Probe Set 403G

| SAMPLE ID | HBV LCR IMX ® | STATISTICS |
|---|---|---|
| Healthy Patients |  | mean = 9.01 ± 5.66 |
| 1 | 4.7 | % CV = 62.8 |
| 2 | 6.4 |  |
| 3 | 4.1 |  |
| 4 | 7.6 |  |
| 5 | 19.7 |  |
| 6 | 6.9 |  |
| 7 | 13.7 |  |
| Non B Hepatitis Patients |  | mean = 5.63 ± 1.52 |
| 8 | 3.7 | % CV = 26.94 |
| 9 | 3.9 |  |
| 10 | 6.2 |  |
| 11 | 5.2 |  |
| 12 | 5.4 |  |
| 13 | 6.6 |  |
| 14 | 4.9 |  |

TABLE 6-continued

Evaluation Of 31 Serum Samples Using HBV Probe Set 403G

| SAMPLE ID | HBV LCR IMX ® | STATISTICS |
|---|---|---|
| 15 | 6.1 |  |
| 16 | 8.7 |  |
| Autoimmune Hepatitis Patients |  | mean = 7.11 ± 4.58 % CV = 64.46 |
| 17 | 6.5 |  |
| 18 | 6.7 |  |
| 19 | 5.8 |  |
| 20 | 6.1 |  |
| 21 | 4.6 |  |
| 22 | 7.8 |  |
| 23 | 10.2 |  |
| 24 | 7.8 |  |
| 25 | 5.6 |  |
| 26 | 4.9 |  |
| 27 | 4.1 |  |
| 28 | 4.6 |  |
| 29 | 3.5 |  |
| 30 | 22.5 |  |
| 31 | 5.9 |  |
| Negative Control | 10.5/19.55 |  |
| Positive Control | 239.1/342.2 |  |

% CV = Coefficient of Variation

Example 6

LCR was performed using probe sets 403G (SEQ ID Nos. 1, 2, 3, and 4) and 184G (SEQ ID Nos. 5, 6, 7, and 8) under conditions described in Example 1, above using twenty human serum samples from different groups of patients with hepatitis B infections (HBsAg+). The results shown in Table 7, below. The samples were tested in two replicates and mean values are shown as signal-to-noise (S/N) ratio. The criteria for evaluation of tested samples (−, ±, + or ++) are defined in terms of IMx® background (bg) rates wherein a 0–1.5×bg rate is defined as negative (−); >1.5–3.0×bg rate as indeterminate (±); 3.0–20×bg rate as weak positive (+); and >20×bg rate as positive (++).

In addition to LCR, the samples were evaluated using Abbott HBV DNA test (DNA solution hybridization assay) and the Polymerase Chain Reaction (PCR). All samples were HBsAg positive and the results of HBeAg or Anti-HBe are included. The tested HBV carriers had different clinical backgrounds. High viremia was characterized by the presence of HBV-DNA and HBeAg; low viremia by the presence of anti-HBe and HBV DNA; and asymptomatic HBV carriers by the presence of anti-HBe.

TABLE 7

Evaluation Of 20 HBV Human Sera

| Sample ID | HBsAg | HBeAg | Anti-HBe | HBV LCR Set 403G (S/N)/result | | HBV LCR Set 184G (S/N)/result | | HBV DNA pg/ml | | PCR Result |
|---|---|---|---|---|---|---|---|---|---|---|
| 5 | + | nd* | nd* | 0.9 | – | 44.5 | + | – | | – |
| 10 | + | – | + | 1.0 | – | 13.1 | + | – | | – |
| 19 | + | nd* | nd* | 1.3 | – | 1.0 | – | – | | – |
| 66 | + | – | + | 3.1 | + | 5.3 | + | – | | – |
| 72 | + | – | +/– | 34.2 | ++ | 51.9 | ++ | – | | –(+)** |
| 26 | + | – | + | 2.0 | ++ | 22.4 | ++ | – | | + |
| 27 | + | + | – | 66.8 | ++ | 273.8 | ++ | – | | + |
| 20 | + | – | +/– | 2.0 | + | 10.2 | + | – | | + |
| 52 | + | – | + | 19.9 | + | 63.6 | + | – | | + |
| 57 | + | + | – | 130.8 | ++ | 369.8 | ++ | – | | + |
| 60 | + | – | + | 300.3 | ++ | 361.4 | ++ | – | | + |
| 64 | + | + | – | 194.9 | ++ | 324.7 | ++ | – | | + |
| 67 | + | – | + | 2.0 | +/– | 2.5 | +/– | – | | + |
| 69 | + | – | + | 22.8 | ++ | 239.3 | ++ | – | | + |
| 70 | + | – | + | 246.3 | ++ | 340.7 | ++ | – | | + |
| 6 | + | nd* | nd* | 323.0 | ++ | 437.9 | ++ | 44 | | + |
| 13 | + | – | + | 231.5 | ++ | 415.7 | ++ | 97 | | + |
| 41 | + | – | + | 335.5 | ++ | 419.1 | ++ | 17 | | + |
| 74 | + | + | – | 3732 | ++ | 455.2 | ++ | 107 | | + |
| 75 | + | + | – | 363.8 | ++ | 446.0 | ++ | 88 | | + |

*nd is "not determined".
**After seeing LCR data and retesting by PCR, it became weak positive.

Example 7

LCR was performed using probe set 403G (SEQ ID Nos. 1, 2, 3, and 4) under conditions described in Example 1 and used to monitor HBV DNA levels in follow-up samples of patients (A, B, C) with chronic liver infections. The LCR data from the IMx® instrument presented as signal-to-noise (S/N) ratio can be compared directly in the graphs with the serum level (m/l) of the liver derived enzyme alanine aminotransaminase (ALT). The criteria for evaluation of tested samples was as described in Example 6, above.

Figure 3A:
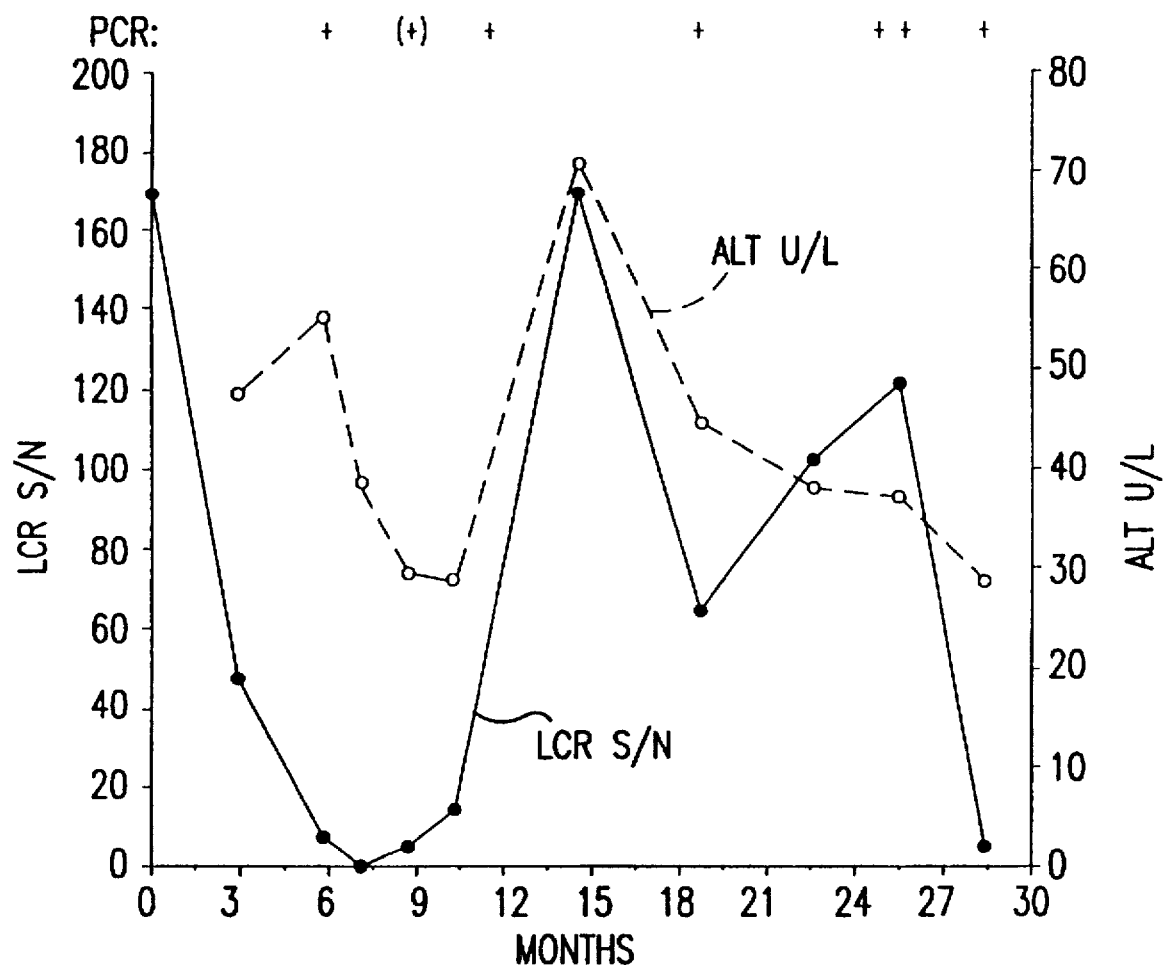
FIGS. 3a–3c are graphs of results obtained from three patients (designated A, B, C) with HBV infection. The data (Example 7) obtained with LCR clearly paralleled the alanine aminotransferase ("ALT") levels semi-quantitatively (FIG. 3 a). HBV-DNA levels could also be determined in samples of serial bleeds of patients receiving interferon treatment (3b–3c). In these patients' sera, HBV-DNA was clearly detectable by conventional dot blot hybridization test before starting interferon treatment but became negative after therapy. In the LCR detection system, serum HBV-DNA could be detected even after successful treatment for several weeks longer than with the conventional hybridization assay.
Figure 3B:
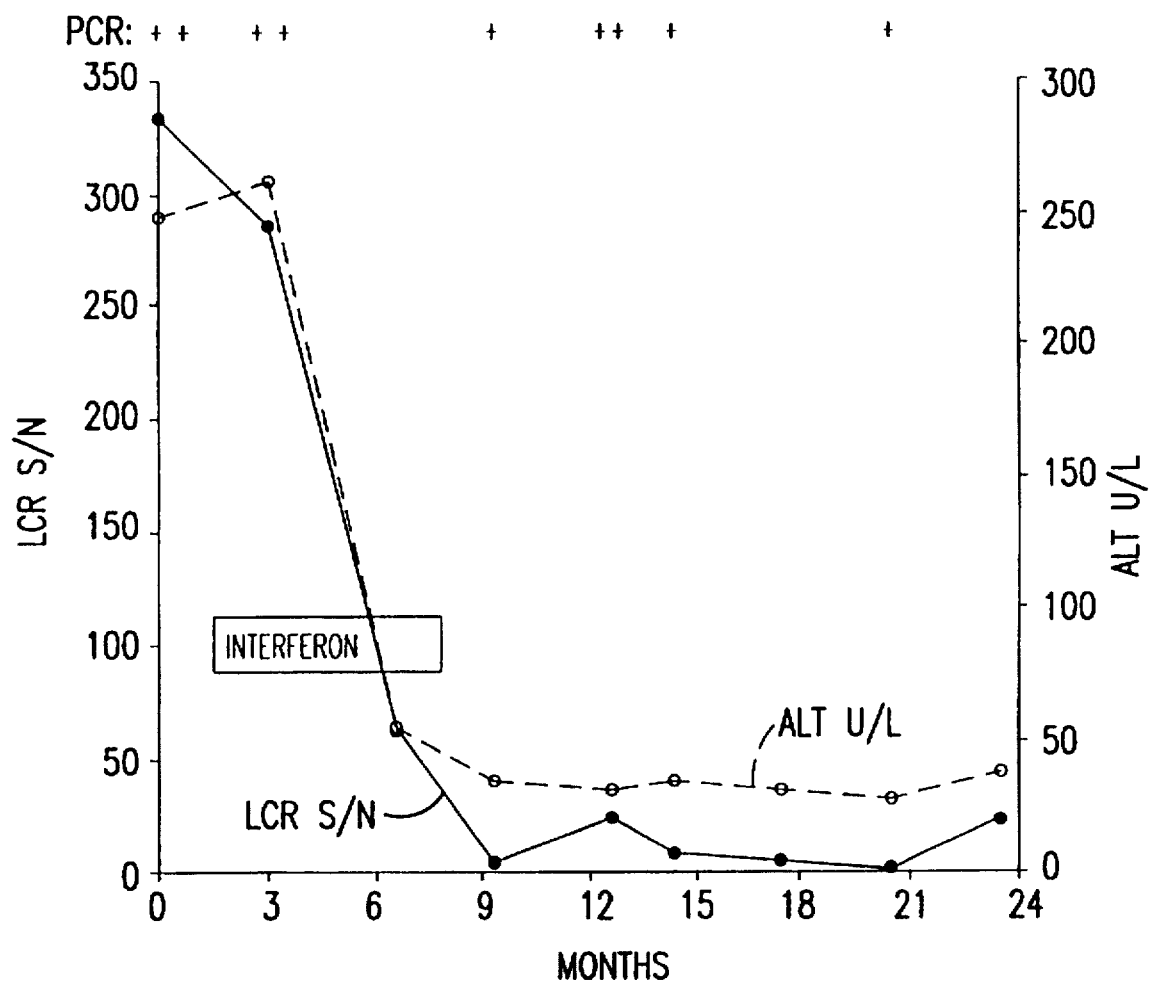
Figure 3C:
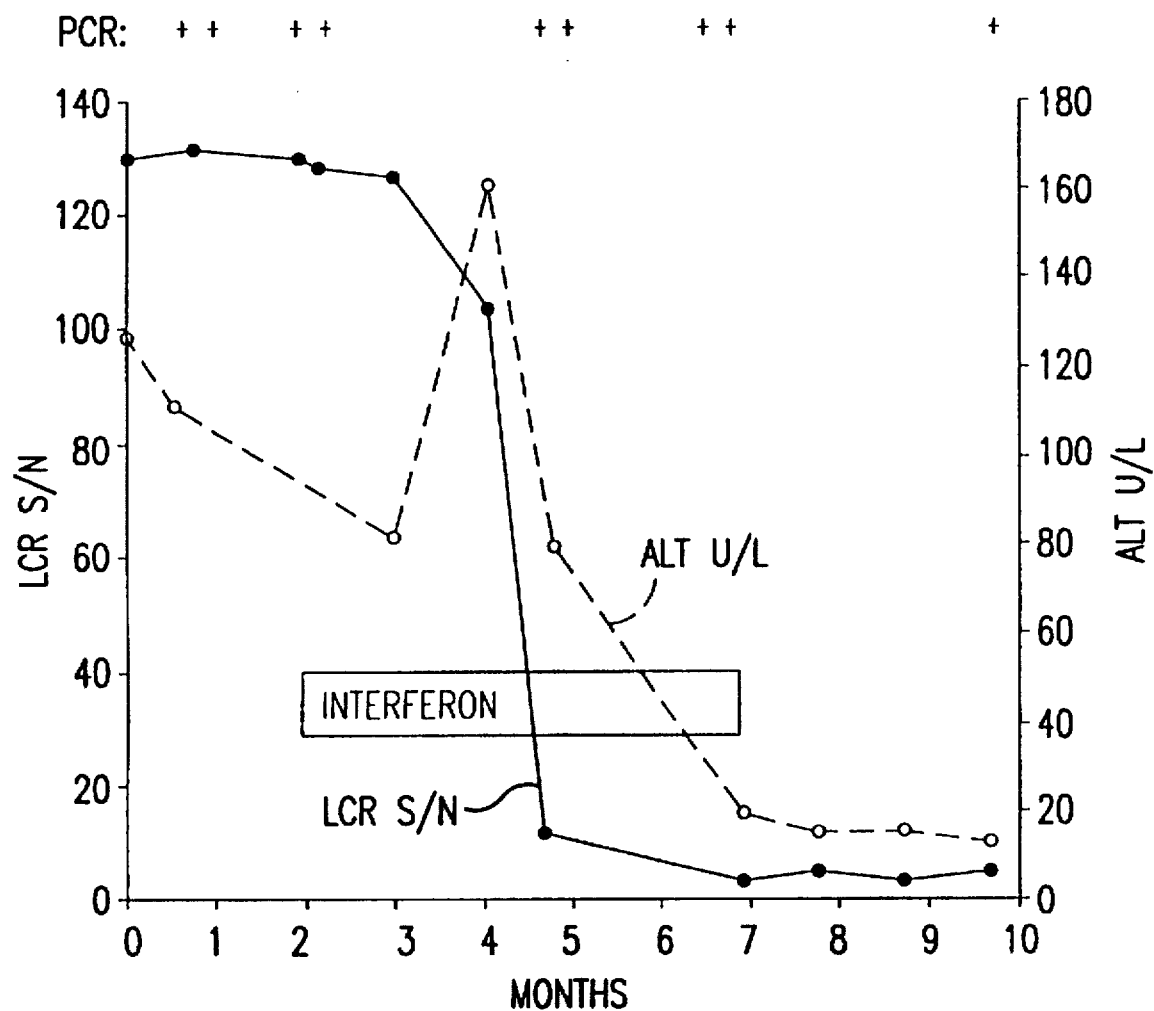

The study was conducted as follows. Patient A received interferon therapy (designated * in table below) on Jun. 13, 1990 and Oct. 15, 1990 (A2 and A3, below); HBV DNA levels were monitored at set intervals through Mar. 17, 1992. Patient C received interferon therapy on Nov. 14, 1991, Dec. 10, 1991, Jan. 7, 1992, Jan. 28, 1992, and Mar. 3, 1992 (C4–C8, below). HBV DNA levels were monitored at set intervals through May 26, 1992. In these patients' sera, HBV-DNA was clearly detectable by conventional dot blot hybridization test before starting interferon treatment but became negative after therapy. In the LCR detection system, serum HBV-DNA could be detected even after successful treatment for several weeks longer than with the conventional hybridization assay. The suitability of semiquantitative monitoring of HBV DNA and ALT by LCR detection is schematically illustrated in FIGS. 3a–3c.

TABLE 8

Serial Serum Samples (Therapy Monitoring)

| Patient | LCR data | LCR result | HBV DNA pg/ml | PCR | HBeAg | a-HBe | ALT m/l |
|---|---|---|---|---|---|---|---|
| A1 | 329.6 | +/+ | 96 | ++ | – | +/– | 248 |
| A2* | 285 | +/+ | 10 | ++ | – | + | 263 |
| A3* | 59.6 | +/+ | nd** | nd** | nd** | nd** | 54 |
| A4 | 2.5 | +/– | nd** | nd** | nd** | nd** | 29 |
| A5 | 18.5 | + | – | ++ | – | + | 28 |
| A6 | 5.5 | + | – | nd | nd** | nd** | 30 |
| A7 | 4.2 | + | – | nd** | nd** | nd** | 28 |
| A8 | 2.1 | +/– | – | + | – | – | 26 |
| A9 | 20.1 | +/+ | – | nd** | – | + | 33 |
| B1 | 31.3 | +/+ | + | nd** | + | – | 32 |
| B2 | 168.7 | +/+ | 15 | nd** | + | – | 48 |
| B3 | 46.2 | +/+ | 6 | nd** | + | – | 48 |
| B4 | 6.8 | + | – | nd** | +/– | +/– | 55 |
| B5 | 2.4 | +/– | – | nd** | – | +/– | 38 |
| B6 | 5.3 | + | – | nd** | +/– | – | 29 |
| B7 | 13.7 | + | – | nd** | + | – | 28 |
| B8 | 166.9 | +/+ | 10 | nd** | + | – | 70 |
| B9 | 62.7 | +/+ | – | nd** | + | – | 44 |
| B10 | 101.0 | +/+ | – | nd** | + | – | 38 |
| B11 | 117.9 | +/+ | nd | ++ | + | – | 37 |

TABLE 8-continued

Serial Serum Samples (Therapy Monitoring)

| Patient | LCR data | LCR result | HBV DNA pg/ml | PCR | HBeAg | a-HBe | ALT m/l |
|---|---|---|---|---|---|---|---|
| B12 | 3.8 | + | – | + | nd** | nd** | 28 |
| C1 | 129.7 | +/+ | 52 | nd** | + | – | 126 |
| C2 | 130.7 | +/+ | 81 | ++ | + | – | 107 |
| C3 | 130.5 | +/+ | nd** | ++ | nd** | nd** | nd** |
| C4* | 128.4 | +/+ | nd** | nd** | nd** | nd** | nd** |
| C5* | 124.9 | +/+ | 70 | nd** | + | – | 79 |
| C6* | 101.6 | +/+ | 12 | nd** | + | – | 159 |
| C7* | 11.1 | + | nd | ++ | + | – | 78 |
| C8* | 3.3 | + | 63 | ++ | + | – | 18 |
| C9 | 4.7 | + | – | nd** | (+) | – | 13 |
| C10 | 4.3 | + | – | nd** | + | – | 14 |
| C11 | 5.9 | + | – | + | + | – | 12 |

\* = patient received interferon therapy
\*\*nd is "not determined"

Example 8

LCR was performed using probe set 403G (SEQ ID Nos. 1, 2, 3, and 4) under conditions described in Example 1, except 0.5 units of DNA polymerase and 3400 units of DNA ligase were used. Reactions were set up either with a HBV DNA negative serum (negative control) or serum containing HBV type adw or type ay.

Following amplification, reactions were diluted 1:1 with IMx® diluent buffer, and the LCR amplification products were detected via a sandwich immunoassay performed using the Abbott IMx® automated immunoassay system. The numerical values given in the following examples are the rate reads of this process, expressed in counts/sec/sec (c/s/s). The amount of ligated probes was directly related to the read rate (as described in European Patent Application No. 357-011). The samples were tested in three replicates; the average values are listed as mean value and the coefficient of variation (CV %) of the three replicates is illustrated in Table 9 below.

TABLE 9

Consensus Detection of HBV Subtypes adw and ay Using Probe Set 403G (SEQ ID Nos. 1, 2, 3, and 4)

| HBV-strains (dilut.)* | mean values c/s/s** | % CV |
|---|---|---|
| HBV adw | | |
| (1:500) | 573.83 | 8.8 |
| (1:250) | 781.53 | 25.1 |
| (1:100) | 1230.42 | 2.4 |
| HBV ay | | |
| (1:500) | 223.80 | 16.7 |
| (1:250) | 282.79 | 53.2 |
| (1:100) | 486.59 | 33.7 |
| neg. contr. | 37.89 | 36.7 |

\*diluted with HBV negative human serum
\*\*each dilution/sample tested in 3 replicates The results indicate that probe set 403G is useful for consensus detection of HBV subtypes and for following patients eligible for or undergoing anti viral therapy.

Example 9

Probes SEQ Id Nos. 1 and 4 were used as primers for the detection of HBV DNA using a modification of Polymerase Chain Reaction (PCR) referred to as "short PCR" or "sPCR". sPCR was performed essentially following the package insert of the commercially available Gene-AMP™ kit available form Perkin-Elmer/Cetus, Emeryville, Calif. Controls were used from the Abbott Genostics™ DNA kit. PCR was run using primer set SEQ ID nos. 1 and 4 at $1\times10^{12}$ molec./reaction, reaction buffer for 30 cycles of: 94° C. for 30 seconds and 50° C. for 20 seconds and Taq Polymerase (Cetus) at 1.25 units per reaction. The duplex product was isolated and detected in an IMx® instrument as described in EP 357,011 to Laffler, et al. published Mar. 7, 1990, which is herein incorporated in its entirety by reference. The average results of duplicate runs are given below.

| PCR with SEQ Id. Nos. 1 and 4 | |
|---|---|
| SAMPLE DNA | IMx ™ rates (mean values) |
| Negative Control | 4.3 |
| Positive control | 1020.0 |
| 5.2 × 10⁵ molecules/mL | 79.3 |
| 1.4 × 10⁷ molecules/mL | 1024.6 |
| 2.8 × 10⁷ molecules/mL | 1143.5 |

Example 10

Probes SEQ Id Nos. 5 and 8 were used as primers for the detection of HBV DNA with PCR as described in Example 9, above. The average results of duplicate runs are given below.

| PCR with SEQ Id. Nos. 5 and 8 | |
|---|---|
| SAMPLE DNA | IMx ® rates (mean values) |
| Negative Control | 6.9 |
| Positive control | 1765.2 |
| 5.2 × 10⁵ molecules/mL | 945.1 |
| 1.4 × 10⁷ molecules/mL | 1736.8 |
| 2.8 × 10⁷ molecules/mL | 1730.3 |

Example 11

Using probes SEQ ID Nos. 1 and 3, target specific polymerization and ligation is performed as described in U.S. Pat. No. 5,185,243 issued Feb. 9, 1993, which is incorporated in its entirety by reference. The probes are derivatized with FITC and/or fluorescein as described above and mixed with selected target HBV DNA, a modified t7 DNA polymerase available from United States Biochemical, Cleveland, Ohio), buffer and water. The mixture is is heated to 80° C. for 5 minutes and is allowed to cool slowly to 23° C. After a brief spin, $^{32}$P-labeled dCTP, T4 DNA ligase, and DNA polymerase are added to the reaction. The resulting solution is incubated at 23° C. for 12 hours. Denaturing polyacrylamide gel electrophoresis of an aliquot from the above reaction shows a $^{32}$P-labeled product of 48 bases in length. This product corresponds to the fill-in and ligation product of SEQ ID Nos. 1 and 3 after hybridization to target.

Example 12

Using probes SEQ ID Nos. 1 and 28 are hybridized to target HBV DNA under conditions described in Example 11, above except dATP and dCTP are added. An aliquot of the reaction n-fixture shows a $^{32}$P-labeled product of 48 bases in length. This product corresponds to the fill-in and ligation product of SEQ ID Nos. 1 and 28 after hybridization to target.

What is claimed is:

1. An oligonucleotide probe specific for hepatitis B virus selected from the group selected from SEQ. ID. Nos. 3, 4, 5, 9, 31 and 32.

2. A method for detecting the presence of hepatitis B virus DNA in a test sample comprising hybridizing a probe of claim 1 to said DNA and detecting the hybridized probe.

3. A kit for detecting hepatitis B virus comprising at least one oligonucleotide according to claim 1, and means for detecting said oligonucleotide.

4. The method of claim 2 further including an amplification step prior to or concurrent with said hybridizing step.

5. The kit according to claim 3 further comprising reagents for amplifying hepatitis B virus DNA in a sample.

6. A composition for detecting hepatitis B virus DNA present in a test sample, said composition comprising a first oligonucleotide probe and a second oligonucleotide probe, wherein said first and second probes are selected from the group consisting of:

(a) SEQ. ID. Nos. 1 and 3;
(b) SEQ. ID. Nos. 5 and 8;
(c) SEQ. ID. Nos. 9 and 11; and
(d) SEQ. ID. Nos. 9 and 32.

7. A method for determining the presence or amount of hepatitis B virus in a test sample comprising:

(a) hybridizing a first and a second oligonucleotide probe according to claim 6 to a hepatitis B virus target sequence;

(b) amplifying said target sequence to form an amplification product; and (c) detecting said amplification product as an indication of the presence or amount of hepatitis B virus in said test sample.

8. A kit for detecting hepatitis B virus comprising:

(a) a first and a second oligonucleotide probe according to claim 6 wherein at least one of said probes is labeled; and (b) a reagent selected from the group consisting of a polymerase, a ligase, or a polymerase and a ligase.

9. The kit of claim 8 further comprising a supply of at least one deoxynucleotide triphosphate.

10. A composition for detecting hepatitis B virus DNA present in a test sample comprising (i) a first set of oligonucleotides comprising a first upstream probe and a first downstream probe hybridizable to the same strand of a hepatitis B virus target sequence and (ii) a second set of oligonucleotides comprising a second downstream probe and second upstream probe both second probes hybridizable to the first set of oligonucleotides wherein said first and second sets of oligonucleotide probes are selected from the probe groups consisting of:

(a) SEQ. ID. NOs. 1, 2, 3 and 4;

(b) SEQ. ID. NOs. 9, 31, 32 and 33; and (c) SEQ. ID. NOs. 9, 10, 11 and 12.

11. A method of detecting the presence or amount of hepatitis B virus in a test sample comprising the steps of:

(a) contacting a test sample with a composition according to claim 10;

(b) correcting one probe from each of said first and second sets of oligonucleotides;

(c) ligating said first upstream probe to said first downstream probe and said second upstream probe to said second downstream probe;

(d) detecting ligated oligonucleotide probes as an indication of the presence or amount of hepatitis B virus in said test sample.

12. A kit for detecting hepatitis B virus in a test sample comprising:

(a) a probe group according to claim 10;

(b) a polymerase; and (c) a ligase.

* * * * *

SEQUENCE LISTING ( 1 ) GENERAL INFORMATION:

( i i i ) NUMBER OF SEQUENCES: 33

( 2 ) INFORMATION FOR SEQ ID NO: 1:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 1:

TTCCTCTTCA TCCTGCTGCT ATG                      23

( 2 ) INFORMATION FOR SEQ ID NO: 2:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 2:

ATAGCAGCAG GATGAAGAGG AA                      22

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 3:

CTCATCTTCT TGTTGGTTCT TCTG                    24

( 2 ) INFORMATION FOR SEQ ID NO: 4:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 4:

CAGAAGAACC AACAAGAAGA TGAGG                    25

( 2 ) INFORMATION FOR SEQ ID NO: 5:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 5:

GACCCCTGCT CGTGTTACAG G                        21

( 2 ) INFORMATION FOR SEQ ID NO:6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 6:

CTGTAACACG AGCAGGGGTC                          20

( 2 ) INFORMATION FOR SEQ ID NO:7:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 7:

GGGGTTTTTC TTGTTGACAA                          20

( 2 ) INFORMATION FOR SEQ ID NO:8:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 8:

TTGTCAACAA GAAAAACCCC G                        21

( 2 ) INFORMATION FOR SEQ ID NO:9:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 9:

CCTCACAATA CCGCAGAGTC TAGA                     24

( 2 ) INFORMATION FOR SEQ ID NO:10:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 10:

AGACTCTGCG GTATTGTGAG GATT                    24

(2) INFORMATION FOR SEQ ID NO:11:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 11:

GTGGTGGACT TCTCTCAATT TTCT                    24

(2) INFORMATION FOR SEQ ID NO:12:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 12:

GAAAATTGAG AGAAGTCCAC CACGAG                  26

(2) INFORMATION FOR SEQ ID NO:13:

(i) SEQUENCE CHARACTERISTICS:
        (A) LENGTH: 23
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 13:

CAAGCTGTGC CTTGGGTGGC TTT                     23

(2) INFORMATION FOR SEQ ID NO:14:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Other nucleic acid (synthetic DNA)

(xi) SEQUENCE DESCRIPTION: SEQ ID NO: 14:

GCCACCCAAG GCACAGCTTG                         20

(2) INFORMATION FOR SEQ ID NO:15:

(i) SEQUENCE CHARACTERISTICS:
        (A) LENGTH: 24
        (B) TYPE: nucleic acid
        (C) STRANDEDNESS: single ( D ) TOPOLOGY: linear ( i i ) MOLECULE TYPE: Other nucleic acid (synthetic DNA)

( x i ) SEQUENCE DESCRIPTION: SEQ ID NO: 15:

GCATGGACAT TGACCCTTAT AAAG     24

( 2 ) INFORMATION FOR SEQ ID NO:16:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 16:

CTTTATAAGG GTCAATGTCC ATGCCCC     27

( 2 ) INFORMATION FOR SEQ ID NO:17:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 17:

CTCTTGGCTC AGTTTACTAG TG     22

( 2 ) INFORMATION FOR SEQ ID NO:18:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 18:

TAGTAAACTG AGCCAAGAGA A     21

( 2 ) INFORMATION FOR SEQ ID NO:19:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 19:

TTTGTTCAGT GGTTCGTAGG G     21

( 2 ) INFORMATION FOR SEQ ID NO:20:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 20:

```
CTACGAACCA CTGAACAAAT GG                                                     22
```

( 2 ) INFORMATION FOR SEQ ID NO:21:

( i ) SEQUENCE CHARACTERISTICS:
        ( A ) LENGTH: 42
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 21:

```
GACCCCTGCT CGTGTTACAG GCGGGGTTTT TCTTGTTGAC AA                                42
```

( 2 ) INFORMATION FOR SEQ ID NO:22:

( i ) SEQUENCE CHARACTERISTICS:
        ( A ) LENGTH: 51
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 22:

```
CCTCACAATA CCGCAGAGTC TAGACTCGTG GTGGACTTCT CTCAATTTTC T                      51
```

( 2 ) INFORMATION FOR SEQ ID NO:23:

( i ) SEQUENCE CHARACTERISTICS:
        ( A ) LENGTH: 48
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 23:

```
TTCCTCTTCA TCCTGCTGCT ATGCCTCATC TTCTTGTTGG TTCTTCTG                          48
```

( 2 ) INFORMATION FOR SEQ ID NO:24:

( i ) SEQUENCE CHARACTERISTICS:
        ( A ) LENGTH: 46
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 24:

```
CTCTTGGCTC AGTTTACTAG TGCCATTTGT TCAGTGGTTC GTAGGG                            46
```

( 2 ) INFORMATION FOR SEQ ID NO:25:

( i ) SEQUENCE CHARACTERISTICS:
        ( A ) LENGTH: 50
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO: 25:

```
CAAGCTGTGC CTTGGGTGGC TTTGGGGCAT GGACATTGAC CCTTATAAAG                        50
```

( 2 ) INFORMATION FOR SEQ ID NO:27:

( i ) SEQUENCE CHARACTERISTICS:
  ( A ) LENGTH: 23
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( i x ) FEATURE:
  ( A ) NAME/KEY: 5'hydroxyl
  ( B ) LOCATION: 1

( x i ) SEQUENCE DESCRIPTION: SEQ ID NO: 27:

AATAGCAGCA GGATGAAGAG GAA    23

( 2 ) INFORMATION FOR SEQ ID NO:28:

( i ) SEQUENCE CHARACTERISTICS:
  ( A ) LENGTH: 25
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( i x ) FEATURE:
  ( A ) NAME/KEY: 5'hydroxyl
  ( B ) LOCATION: 1

( x i ) SEQUENCE DESCRIPTION: SEQ ID NO: 28:

ACTCATCTTC TTGTTGGTTC TTCTG    25

( 2 ) INFORMATION FOR SEQ ID NO:31:

( i ) SEQUENCE CHARACTERISTICS:
  ( A ) LENGTH: 27
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( i x ) FEATURE:
  ( A ) NAME/KEY: 5'hydroxyl
  ( B ) LOCATION: 1

( x i ) SEQUENCE DESCRIPTION: SEQ ID NO: 31:

ACTAGACTCT GCGGTATTGT GAGGATT    27

( 2 ) INFORMATION FOR SEQ ID NO:32:

( i ) SEQUENCE CHARACTERISTICS:
  ( A ) LENGTH: 27
  ( B ) TYPE: nucleic acid
  ( C ) STRANDEDNESS: single
  ( D ) TOPOLOGY: linear ( i i ) MOLECULE TYPE: Other nucleic acid (synthetic DNA)

( i x ) FEATURE:
  ( A ) NAME/KEY: 5'hydroxyl
  ( B ) LOCATION: 1

( x i ) SEQUENCE DESCRIPTION: SEQ ID NO: 32:

ATCGTGGTGG ACTTCTCTCA ATTTTCT    27

( 2 ) INFORMATION FOR SEQ ID NO:33:

( i ) SEQUENCE CHARACTERISTICS:
  ( A ) LENGTH: 25
  ( B ) TYPE: nucleic acid

```
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 33:

AAAATTGAGA GAAGTCCACC ACGAG                                                      2 5

( 2 ) INFORMATION FOR SEQ ID NO:35:

( i ) SEQUENCE CHARACTERISTICS:
            ( A ) LENGTH: 23
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( i x ) FEATURE:
            ( A ) NAME/KEY: 5'hydroxyl
            ( B ) LOCATION: 1

( x i ) SEQUENCE DESCRIPTION: SEQ ID NO: 35:

TCACTAGTAA ACTGAGCCAA GAG                                                        2 3

( 2 ) INFORMATION FOR SEQ ID NO:36:

( i ) SEQUENCE CHARACTERISTICS:
            ( A ) LENGTH: 22
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( i x ) FEATURE:
            ( A ) NAME/KEY: 5'hydroxyl
            ( B ) LOCATION: 1

( x i ) SEQUENCE DESCRIPTION: SEQ ID NO: 36:

ACATTGTTC AGTGGTTCGT AG                                                          2 2

( 2 ) INFORMATION FOR SEQ ID NO:37:

( i ) SEQUENCE CHARACTERISTICS:
            ( A ) LENGTH: 21
            ( B ) TYPE: nucleic acid
            ( C ) STRANDEDNESS: single
            ( D ) TOPOLOGY: linear ( i i ) MOLECULE TYPE: Other nucleic acid (synthetic DNA)

( x i ) SEQUENCE DESCRIPTION: SEQ ID NO: 37:

CTACGAACCA CTGAACAAAT G                                                          2 1
```